United States Patent
Cinader, Jr. et al.

(10) Patent No.: US 9,480,540 B2
(45) Date of Patent: Nov. 1, 2016

(54) BONDABLE DENTAL ASSEMBLIES AND METHODS INCLUDING A COMPRESSIBLE MATERIAL

(75) Inventors: David K. Cinader, Jr., Walnut, CA (US); Ma Thazin Aung, Duarte, CA (US); Lee C. Yick, Temple City, CA (US); James D. Cleary, Glendora, CA (US)

(73) Assignee: 3M Innovative Properties Company, St. Paul, MN (US)

( * ) Notice: Subject to any disclaimer, the term of this patent is extended or adjusted under 35 U.S.C. 154(b) by 34 days.

(21) Appl. No.: 13/976,393

(22) PCT Filed: Dec. 12, 2011

(86) PCT No.: PCT/US2011/064356
§ 371 (c)(1),
(2), (4) Date: Jun. 26, 2013

(87) PCT Pub. No.: WO2012/091902
PCT Pub. Date: Jul. 5, 2012

(65) Prior Publication Data
US 2013/0280669 A1  Oct. 24, 2013

Related U.S. Application Data

(60) Provisional application No. 61/428,498, filed on Dec. 30, 2010.

(51) Int. Cl.
*A61C 3/00* (2006.01)
*A61C 7/16* (2006.01)
(Continued)

(52) U.S. Cl.
CPC . *A61C 7/16* (2013.01); *A61C 7/14* (2013.01); *A61K 6/0023* (2013.01); *A61C 2202/00* (2013.01); *A61C 2202/01* (2013.01)

(58) Field of Classification Search
CPC ....... A61C 2202/01; A61C 7/14; A61C 7/16
USPC ....... 433/9, 24, 173–174, 201.1; 156/43, 78, 156/79, 145; 128/206.14, 206.25; 264/177.11, 413, 36.11, 48, 628, 264/288.8, 916; 427/464, 505, 516, 207.1, 427/208.2, 208.4
See application file for complete search history.

(56) References Cited

U.S. PATENT DOCUMENTS 3,018,262 A  1/1962  Schroeder
4,259,075 A  3/1981  Yamauchi
(Continued)

FOREIGN PATENT DOCUMENTS

CN  201684030  12/2010
EP  0173567  3/1986
(Continued)

OTHER PUBLICATIONS

Nacht,"The Microsponge: A Novel Topical Programmable Delivery System," Drugs and the pharmaceutical sciences, 1990, vol. 42, pp. 299-325.
(Continued)

*Primary Examiner* — Cris L Rodriguez
*Assistant Examiner* — Mirayda A Aponte

(57) ABSTRACT

Dental assemblies and related methods of making are provided. The dental assemblies include a dental article with a bonding surface an adhesive having both a compressible material and at least one hardenable dental composition extending across the bonding surface. The compressible material is coupled to the dental article by a first quantity of hardened dental composition extending at least partially through the compressible material and contacting the bonding surface. The hardened dental composition extends over less than the entire bonding surface. Adjacent portions of the compressible material contain a second quantity of unhardened dental composition, preserving flexibility of the compressible material. Advantageously, this configuration was found to enhance bond reliability and facilitate manufacturing.

14 Claims, 3 Drawing Sheets

(51) Int. Cl.
  *A61C 7/14* (2006.01)
  *A61K 6/00* (2006.01)

(56) References Cited

U.S. PATENT DOCUMENTS

| | | | |
|---|---|---|---|
| 4,298,738 A | 11/1981 | Lechtken |
| 4,303,730 A | 12/1981 | Torobin |
| 4,324,744 A | 4/1982 | Lechtken |
| 4,336,338 A | 6/1982 | Downs |
| 4,356,296 A | 10/1982 | Griffith |
| 4,385,109 A | 5/1983 | Lechtken |
| 4,499,251 A | 2/1985 | Omura |
| 4,503,169 A | 3/1985 | Randklev |
| 4,537,940 A | 8/1985 | Omura |
| 4,539,382 A | 9/1985 | Omura |
| 4,605,402 A | 8/1986 | Iskra |
| 4,642,126 A | 2/1987 | Zador |
| 4,648,843 A | 3/1987 | Mitra |
| 4,652,274 A | 3/1987 | Boettcher |
| 4,665,217 A | 5/1987 | Reiners |
| 4,695,251 A | 9/1987 | Randklev |
| 4,710,523 A | 12/1987 | Lechtken |
| 4,737,593 A | 4/1988 | Ellrich |
| 4,752,338 A | 6/1988 | Reiners |
| 4,865,596 A | 9/1989 | Weisman |
| 4,872,936 A | 10/1989 | Engelbrecht |
| 4,978,007 A | 12/1990 | Jacobs |
| 5,015,180 A | 5/1991 | Randklev |
| 5,026,902 A | 6/1991 | Fock |
| 5,037,861 A | 8/1991 | Crivello |
| 5,045,569 A | 9/1991 | Delgado |
| 5,063,257 A | 11/1991 | Akahane |
| 5,076,844 A | 12/1991 | Fock |
| 5,108,285 A | 4/1992 | Tuneberg |
| 5,130,347 A | 7/1992 | Mitra |
| 5,154,762 A | 10/1992 | Mitra |
| 5,172,809 A | 12/1992 | Jacobs |
| 5,176,951 A | 1/1993 | Rudo |
| 5,227,413 A | 7/1993 | Mitra |
| 5,269,680 A | 12/1993 | Kawaguchi |
| 5,328,363 A | 7/1994 | Chester |
| 5,367,002 A | 11/1994 | Huang |
| 5,501,727 A | 3/1996 | Wang |
| 5,520,725 A | 5/1996 | Kato |
| 5,530,038 A | 6/1996 | Yamamoto |
| 5,545,676 A | 8/1996 | Palazzotto |
| 5,614,570 A | 3/1997 | Hansen |
| 5,770,636 A | 6/1998 | Wernsing |
| 5,817,704 A | 10/1998 | Shiveley |
| 5,846,640 A | 12/1998 | Vallittu |
| 5,856,373 A | 1/1999 | Kaisaki |
| 5,859,089 A | 1/1999 | Qian |
| 5,861,214 A | 1/1999 | Kitano |
| 5,871,360 A | 2/1999 | Kato |
| 5,925,715 A | 7/1999 | Mitra |
| 5,962,550 A | 10/1999 | Akahane |
| 5,965,632 A | 10/1999 | Orlowski |
| 6,027,795 A | 2/2000 | Kabra |
| 6,030,606 A | 2/2000 | Holmes |
| 6,084,004 A | 7/2000 | Weinmann |
| 6,089,861 A | 7/2000 | Kelly |
| 6,183,249 B1 | 2/2001 | Brennan |
| 6,187,833 B1 | 2/2001 | Oxman |
| 6,187,836 B1 | 2/2001 | Oxman |
| 6,213,767 B1 | 4/2001 | Dixon |
| 6,245,828 B1 | 6/2001 | Weinmann |
| 6,251,963 B1 | 6/2001 | Kohler |
| 6,331,080 B1 | 12/2001 | Cole |
| 6,387,981 B1 | 5/2002 | Zhang |
| 6,444,725 B1 | 9/2002 | Trom |
| 6,458,868 B1 | 10/2002 | Okada |
| 6,528,555 B1 | 3/2003 | Nikutowski |
| 6,572,693 B1 | 6/2003 | Wu |
| 6,645,618 B2 | 11/2003 | Hobbs |
| 6,669,927 B2 | 12/2003 | Trom |
| 6,670,436 B2 | 12/2003 | Burgath |
| 6,750,261 B1 | 6/2004 | Clear |
| 6,765,036 B2 | 7/2004 | Dede |
| 6,765,038 B2 | 7/2004 | Mitra |
| 6,779,656 B2 | 8/2004 | Klettke |
| 6,982,288 B2 | 1/2006 | Mitra |
| 7,090,721 B2 | 8/2006 | Craig |
| 7,090,722 B2 | 8/2006 | Budd |
| 7,137,812 B2 | 11/2006 | Cleary |
| 7,156,911 B2 | 1/2007 | Kangas |
| 7,173,074 B2 | 2/2007 | Mitra |
| 7,262,228 B2 | 8/2007 | Oxman |
| 7,449,499 B2 | 11/2008 | Craig |
| 7,452,924 B2 | 11/2008 | Aasen |
| 2003/0114553 A1 | 6/2003 | Karim |
| 2003/0196914 A1 | 10/2003 | Tzou |
| 2004/0151691 A1 | 8/2004 | Oxman |
| 2004/0206932 A1 | 10/2004 | Abuelyaman |
| 2005/0133384 A1 | 6/2005 | Cinader |
| 2005/0136370 A1 | 6/2005 | Brennan |
| 2005/0175966 A1 | 8/2005 | Falsafi |
| 2005/0256223 A1 | 11/2005 | Kolb |
| 2006/0096911 A1 | 5/2006 | Brey |
| 2006/0207893 A1 | 9/2006 | Cinader |
| 2006/0208393 A1 | 9/2006 | Karmaker |
| 2006/0257821 A1 | 11/2006 | Cinader |
| 2007/0248927 A1 | 10/2007 | Luchterhandt |
| 2008/0096150 A1* | 4/2008 | Cinader ............ 433/9 |
| 2008/0145820 A1 | 6/2008 | Karmaker |
| 2008/0250974 A1 | 10/2008 | Jia |
| 2009/0011388 A1 | 1/2009 | Craig |
| 2009/0035728 A1 | 2/2009 | Aasen |
| 2009/0065961 A1 | 3/2009 | Teo |
| 2009/0233252 A1 | 9/2009 | Cinader, Jr. |

FOREIGN PATENT DOCUMENTS

| | | |
|---|---|---|
| EP | 63170437 | 7/1988 |
| EP | 712622 | 5/1996 |
| EP | 1051961 | 11/2000 |
| RU | 2246916 | 2/2005 |
| WO | WO 00/38619 | 7/2000 |
| WO | WO 00/42092 | 7/2000 |
| WO | WO 01/07444 | 2/2001 |
| WO | WO 01/30305 | 5/2001 |
| WO | WO 01/30306 | 5/2001 |
| WO | WO 01/30307 | 5/2001 |
| WO | WO 01/51540 | 7/2001 |
| WO | WO 01/92271 | 12/2001 |
| WO | WO 03/063804 | 8/2003 |
| WO | WO 2008/000917 | 1/2008 |
| WO | WO 2008/076739 A2 | 6/2008 |
| WO | WO 2009/045752 | 4/2009 |
| WO | WO 2010/039395 | 4/2010 |
| WO | WO 2011/005276 | 1/2011 |
| WO | WO 2011/153039 | 12/2011 |

OTHER PUBLICATIONS

Akin-Nergiz, "The shearing strength of titanium brackets depending on the coating procedure" Fortschritte der Kieferorthopadie, 1995, vol. 56, No. 1, pp. 49-55.

Atsu, "Effects of Silica Coating and Silane Surface Conditioning on the Bond Strength of Metal and Ceramic Brackets to Enamel", Angle Orthodontist, 2006 vol. 76, No. 5, pp. 857-862.

Davies, "The Separation of Airborne Dust and Particles," Institution of Mechanical Engineers, London Proceedings (B), 1952, vol. 1B, No. 5, pp. 185-198.

Lee, "Handbook of Epoxy Resins", 1967, 3 pages.

International Search Report for PCT International Application No. PCT/US2011/064356, mailed on May 30, 2012, 6 pages.

Mathis, "Properties of a New Glass Ionomer/Composite Resin Hybrid Restorative", Abstract No. 51, Journal of Dental Research, 1987, vol. 66, p. 113.

(56) References Cited

OTHER PUBLICATIONS

Mujagic, "Digital Design and Manufacturing of the Lingualcare Bracket", journal of Clinical Orthodontics, 2005, vol. 39, No. 6, pp. 375-382.

Newman, "Adhesion promoters, their effect on the bond strength of metal brackets", American Journal of Orthodontics and Dentofacial Orthopedics, Sep. 1995, vol. 108, No. 3, pp. 237-241.

Weichmann, "Lingual Orthodontics Part3: Intraoral Sandblasting and Indirect Bonding", Journal of Orofacial Orthopedics, 2000, vol. 61, No. 4, pp. 280-291.

Westerman, "Effect of ethylene vinyl acetate (EVA) closed cell foam on transmitted forces in mouthguard material," British Journal of Sports Medicine, 2002, vol. 36, No. 3, pp. 205-208.

* cited by examiner

BONDABLE DENTAL ASSEMBLIES AND METHODS INCLUDING A COMPRESSIBLE MATERIAL

1. FIELD OF THE INVENTION

Provided are assemblies and related methods for dental applications. More particularly, assemblies and related methods are provided for bonding dental articles to the surfaces of teeth.

2. DESCRIPTION OF THE RELATED ART

Applications in the field of dentistry that involve the bonding of dental articles to teeth are numerous and diverse. One such application is in the specialized field of orthodontics. Orthodontics is the area of dentistry concerned with correction and guidance of a patient's crooked teeth into proper positions. Benefits of such treatment include improved bite function, hygiene, and aesthetics.

Orthodontic therapy commonly uses dental articles (or appliances) that are temporarily bonded to the patient's teeth during the course of treatment. In a type of orthodontic treatment known as fixed appliance therapy, appliances called brackets are affixed to the surfaces of a patient's teeth. Other appliances, called molar tubes, are generally affixed to the patient's posterior (molar) teeth. To initiate treatment, a resilient "U"-shaped archwire of stainless steel or a shape memory alloy is placed into the slots of the brackets, with the terminal ends of the wire received in the molar tubes. Although the archwire is initially deflected when engaged to the brackets and molar tubes, it gradually returns toward its original shape over time. In this manner, the relaxation of the archwire induces the teeth to move from their initial positions to their prescribed positions.

It is common practice to use adhesives to bond orthodontic appliances to teeth. The adhesive is generally coated onto the bonding surfaces of an appliance. After the appliance is mounted onto a tooth, the adhesive is hardened to produce a strong bond. A suitable orthodontic adhesive should provide a high degree of strength to maintain a consistent and secure bond between the appliances and the teeth throughout the course of orthodontic treatment, which can last for two years or more. However, the adhesive bond should not be so aggressive that the appliances become unduly difficult to remove at the end of treatment. An ideal adhesive should also have the proper degree of tack and viscosity to avoid drifting after placing the appliance on the tooth and facilitate handling by the orthodontic practitioner.

Conventional adhesives are polymer resins loaded with a significant amount of a hard filler, such as a quartz or silica filler. In a bonding procedure, an excess of adhesive is usually applied to the bonding surface of the appliance because the adhesive needs to serve as a gap filler. When there is a deviation between the teeth surface and the bonding surface of the appliance, the adhesive fills the space between the appliance and tooth to maintain the bond and prevent formation of voids, which can trap food and plaque. When the appliance is fully seated against the tooth, excess adhesive is expressed along the periphery of the base. This excess adhesive, known as "flash," is manually removed by the practitioner prior to hardening the adhesive.

The presence of adhesive flash can be disadvantageous. Removal of flash is time consuming, especially since accidental perturbation of the appliance can negatively impact bond reliability. Further, incomplete removal of the excess adhesive is problematic. Incomplete removal is especially common in the posterior region and behind hooked appliances, where access is limited. If not fully removed, excess adhesive provides sites for bacteria accumulation. Such bacteria can attack and degrade of the underlying tooth structure, leading to decalcification and discoloration of the teeth. Further, exposed adhesive surfaces are prone to staining from food or drink. Finally, the presence of hard fillers makes removal of the adhesive, once hardened, difficult and uncomfortable to the patient.

Improved assemblies, methods, and kits that use compressible materials have been disclosed in U.S. Publication No. 2008/0096150 (Cinader). These can be advantageously applied in bonding dental articles like orthodontic appliances to teeth. For example, a compressible material capable of filling the gap between the surface of the base of an orthodontic appliance and a tooth structure may be combined with an unfilled or lightly-filled hardenable dental composition to provide an orthodontic adhesive. When an appliance coated with this combination is seated onto the tooth, excess dental composition is forced out of the compressible material in lateral directions, while the compressible material is retained between the appliance and the tooth. Advantageously, no flash clean up is necessary. Since the excess dental composition is unfilled or lightly filled, it can be retained on the tooth and be removed by patient toothbrushing in due course.

3. SUMMARY OF THE INVENTION

Multi-component systems that use compressible materials disclosed in U.S. Publication No. 2008/0096150 (Cinader) represent an important advancement in the art. However, there is a continuing interest in ensuring that such concepts can be used with a wide variety of articles, dental compositions, and compressible materials. Of particular interest are methods of attachment of the combination of the compressible material and dental composition to the dental article. Dental articles generally have undercut features to allow secure bonding to particular dental articles in a wide variety of circumstances. Orthodontic appliances generally have bonding base surfaces with undercut features that provide adequate bond strength through mechanical retention.

In one aspect, a method of making a dental assembly is provided. The method comprises: placing a compressible material in contact with an outer base surface of a dental article; applying a first quantity of an unhardened dental composition to at least one of the compressible material and the outer base surface in such a manner that at least some of the unhardened dental composition is located between the outer base surface and the compressible material; hardening at least a portion of the first quantity of dental composition in order to secure the compressible material to the outer base surface, wherein at least part of the outer base surface is not in contact with the hardened dental composition; and applying a second quantity of unhardened dental composition to the compressible material, wherein the second quantity at least partially surrounds the first quantity as viewed from a direction perpendicular to the outer base surface.

In another aspect, a method of making a dental assembly is provided comprising: providing a dental article having an outer base surface adapted for bonding to a tooth; applying a first quantity of unhardened dental composition to a portion of the outer base surface less than the entire outer base surface; placing a compressible material in contact with the first quantity as well as the outer base surface; hardening the first quantity to secure the compressible material to the dental article; and applying a second quantity of unhardened dental composition to the compressible material wherein the second quantity at least partially surrounds the first quantity as viewed from a direction perpendicular to the outer base surface.

In still another aspect, a method of making an assembly is provided comprising: providing a dental article having an outer base surface adapted for bonding to a tooth; placing a compressible material in contact with the outer base surface; applying an unhardened dental composition to at least a portion of the compressible material and the outer base surface; and hardening dental composition extending over a portion of the outer base surface having an area less than the area of the entire outer base surface to secure the compressible material to the dental article, wherein at least some dental composition not extending over the portion of the outer base surface remains unhardened.

In yet another aspect, a dental assembly is provided comprising: a dental article having an outer base surface adapted for bonding to a tooth; a compressible material contacting and extending across at least a portion of the outer base surface; a hardened dental composition absorbed into the compressible material and contacting a portion of the outer base surface that is less than the entire outer base surface; and an unhardened dental composition absorbed into the compressible material and at least partially surrounding the hardened composition as viewed from a direction perpendicular to the outer base surface.

Limiting the areal coverage of the hardened dental composition with respect to the surface area of the dental article provides several surprising advantages. First, the flexibility of the compressible material is largely retained, leading to improved conformability of the adhesive assembly with the tooth surface during bonding. Second, this configuration allows the dental composition used to secure the compressible material to the dental article to be partially or fully encapsulated by the unhardened dental composition. This, in turn, reduces or eliminates interfacial boundaries that can act as failure interfaces at the edges of the surface area of the dental article, thereby enhancing bond reliability. Third, these methods allow the thickness of the compressible material to be customized over the surface area, thereby improving conformity of the adhesive assembly to the tooth surface during bonding. Finally, these methods significantly facilitate manufacturing of these dental assemblies.

4. BRIEF DESCRIPTION OF THE DRAWINGS

5. DETAILED DESCRIPTION OF THE PREFERRED EMBODIMENTS

Figure 1:
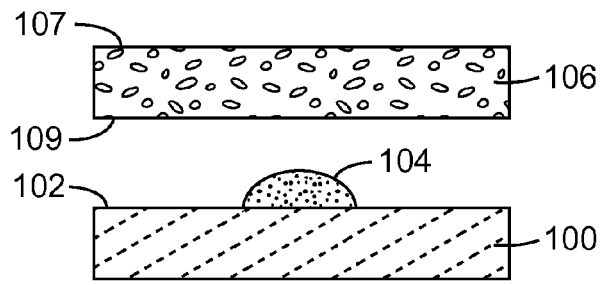
FIG. 1 is a side cross-sectional view of certain components of a dental assembly according to one embodiment of the invention.

Assemblies and methods as described herein include a compressible material that can fill the gap between the surface of a dental article (e.g., the base of an orthodontic appliance) and a tooth structure. Assemblies and methods as described herein optionally include the combination of the compressible material and a hardenable dental composition that can advantageously be unfilled or lightly filled. The combination of the compressible material and the unfilled or lightly filled hardenable dental composition can provide adequate handling properties for application and adequate adhesive properties upon hardening, while allowing for simplified removal, if desired, of excess dental composition by the practitioner. Alternatively, such excess unfilled or lightly filled hardenable or hardened dental composition can typically be removed within a few days by brushing.

Assemblies and methods of the present invention include a compressible material that becomes a part of the bond upon applying the dental article to a tooth structure and hardening a hardenable dental composition. As used herein, a "compressible material" is a material that is reduced in volume upon application of pressures typically employed to place and/or position a dental article on a tooth structure. Forces typically employed to place and/or position a dental article on a tooth structure are 0.5 to 5 pound-force applied to a bonding base of area 0.0164 square inch, corresponding to calculated pressures of 0.2 to 2.0 megapascals (MPa). The ratio of the compressed volume/initial volume (i.e., compressibility) will vary depending on the compressible material used. However, the compressibility is typically 0.9 to 0.001, in certain embodiments 0.7 to 0.01, and in other certain embodiments 0.5 to 0.1.

As used herein, compressible materials can include elastic and/or inelastic materials. Elastic compressible materials include materials that substantially rebound (e.g., rebound to at least to 99% of the initial volume), preferably within 30 seconds at, for example, room temperature or oral temperature, after release of the pressure used to compress the material. Examples of elastic compressible materials include, but are not limited to, polymeric foams, elastic scrims, elastic nonwovens, and combinations thereof.

Inelastic compressible materials are materials that do not substantially rebound, i.e., rebound to at most 50%, in certain embodiments at most 25%, 10%, or even 5% of the initial volume, preferably within 30 seconds at, for example, room temperature or oral temperature, after release of the pressure used to compress the material. Examples of inelastic compressible materials include, but are not limited to, brittle materials (e.g., crosslinked polymeric foams, glass bubbles, glass fibers, ceramic fibers, and combinations thereof) and other materials having no rebound (e.g., dead-soft materials, i.e., the most soft and malleable state of a material). Examples of materials having substantially no rebound include, but are not limited to, foams having substantially no rebound, fibers and/or fiber mats having substantially no rebound, materials having voids in which the voids are at least partially collapsed upon compression (e.g., collapsible honeycomb structures made from paper, polymers, and/or polymeric foams), fabric knit structures, and combinations thereof. For some embodiments, an inelastic compressible material can be advantageous in that the pressure used to compress the compressible material need not be maintained after the dental article is placed and/or positioned on the tooth structure (e.g., prior to and/or during hardening and/or curing of the dental composition).

A wide variety of compressible materials can be used in assemblies and methods of the present invention, including, for example, porous materials, foamed materials, and materials including capsules. The compressible material can be a hydrophilic material, a hydrophobic material, or combinations thereof. The compressible material can be any color, with white or off-white colored compressible materials being preferred for certain embodiments. In certain embodiments, an opaque or colored compressible material can aid in visualization of any material remaining on the tooth surface after the appliance has been removed. The compressible material can be of uniform on non-uniform thickness. The compressible material can be in the form of a layer (e.g., a single layer or multi-layer). Multi-layer compressible materials can include layers that are the same and/or layers that differ from one another.

Assemblies including a compressible material can further include additional components in contact with the compressible material. For example, the assembly can further include a water scavenger (e.g., precipitated silica and/or molecular sieves) in contact with the compressible material to enhance water tolerance during use. For another example, the assembly can further include filler (e.g., fluoroaluminosilicate glass particulates) in contact with (e.g., embedded in or bonded to) the compressible material to modify physical and adhesive characteristics of the compressible material.

In some embodiments, the compressible material is or includes a foamed, hardenable dental composition that is optionally partially hardened, such as a dental adhesive or primer. For example, methacrylate-containing hardenable dental compositions can be foamed using hydrocarbon blowing agents (e.g., propane, isobutane, or combinations thereof such as a 1:1 mixture by weight of propane and isobutane).

For embodiments in which the compressible material is a porous material, a wide variety of porous materials can be used in assemblies and methods of the present invention. As used herein, a "porous material" is a material that includes pores (e.g., voids and/or vessels). In preferred embodiments, the pores are in communication with one another such that a material contained therein (e.g., a hardenable dental composition) can pass between pores (e.g., percolate), for example, during compression of the porous material. In such embodiments, the surface energy of the porous material and the hardenable dental composition can be selected, for example, to have small differences, such that the hardenable dental composition can wet out the compressible material to aid in the retention of the hardenable dental composition in the porous material prior to hardening, and to provide for enhanced mechanical properties and hydrolytic stability.

Exemplary porous materials include foams (e.g., polymeric foams including, for example, cellulose foams, glass foams, polymeric foams, and combinations thereof), sponges, nonwoven fabrics, glass fibers (e.g., glass wool), ceramic fibers, cotton fibers, cellulose fibers, woven mats, nonwoven mats, scrims, and combinations thereof. Exemplary materials are described, for example, in U.S. Pat. No. 4,605,402 (Iskra), U.S. Pat. No. 4,865,596 (Weisman et al.), U.S. Pat. No. 5,614,570 (Hansen et al.), U.S. Pat. No. 6,027,795 (Kabra et al.), U.S. Pat. No. 6,645,618 (Hobbs et al.); Japanese Patent No. JP63170437 (Sakadou et al.); and Nacht et al., "The microsponge: a novel topical programmable delivery system," in *Topical Drug Delivery Formulations*, D. W. Osborn and A. H. Amman (Eds.), Marel Dekker, New York, pp. 299-325 (1990).

For embodiments in which the compressible material includes fibers, the fibers can optionally be tied together (e.g., using a reactive silane, a curable resin, or a colloidal silica) to form a mat or scrim. In certain embodiments, mats can be prepared, for example, using short chopped glass or other fiber loosely bound. Optionally, the fibers can be temporarily encapsulated into a sheet or web to aid in cutting and handling using, for example, a water soluble or dispersible encapsulant (e.g., polyvinyl alcohol). In such embodiments, the mat can be cut into a desired shape and attached to an outer base surface of a bracket, and the temporary encapsulant can then be washed away. In certain embodiments, nonwoven structures can be used as carriers for loading a reinforcing material (e.g., short chopped fibers) to enhance the strength of the composite formed upon curing.

Optionally, a meltblown fiber forming process is used to prepare the compressible material. A standard meltblown fiber forming process is disclosed in commonly assigned U.S. Patent Publication No. 2006/0096911 (Brey et al.). Blown microfibers (BMF) are created by a molten polymer entering and flowing through a die, the flow being distributed across the width of the die in the die cavity and the polymer exiting the die through a series of orifices as filaments. In one embodiment, a heated air stream passes through air manifolds and an air knife assembly adjacent to the series of polymer orifices that form the die exit (tip). This heated air stream can be adjusted for both temperature and velocity to attenuate (draw) the polymer filaments down to the desired fiber diameter. The BMF fibers are conveyed in this turbulent air stream towards a rotating surface where they collect to form a web.

Conventionally, "blown microfibers"—which are discrete, very fine, discontinuous fibers prepared by extruding liquified fiber-forming material through fine orifices in a die into a high-velocity gaseous stream, where the extruded material is first attenuated by the gaseous stream and then solidifies as a mass of the fibers—are collected on a small-mesh wire screen moved transversely through the gaseous stream. The openings in the screen permit passage of a portion of the gaseous stream, but the fibers collect on the screen as a flat, or constant-thickness, coherent web. The web is most often used in its collected form after being removed from the collection screen and cut to useful sizes.

In certain embodiments, the compressible material can include fibers that include all or a portion of a hardenable dental composition (e.g., fluoroaluminosilicate glass fiber).

Polymeric foams can include open-celled foams as described, for example, in U.S. Pat. No. 5,770,636 (Wernsing et al.) and U.S. Pat. No. 5,817,704 (Shively et al.); closed-celled foams as described, for example, in Westerman et al., *British Journal of Sports Medicine*, 36:205-208 (2002); or combinations thereof. Alternatively, closed-cell foams may be converted into porous fibrous articles if oriented and microfibrillated as described, for example, in U.S. Pat. No. 6,645,618 (Hobbs et al.). The hydrophilic/lipophilic balance at the surface of the foam structure can be modified, for example, using polyelectrolytes or functionalized particles during preparation as described, for example, in U.S. Pat. No. 6,750,261 (Clear et al.). In some embodiments, the foam can be surface modified by thermal, chemical (e.g., acid-etching, corona treatment, plasma etching, glow discharge, or flame treatment), and/or photo-chemical (e.g., ultraviolet irradiation) means.

In certain embodiments, the polymeric foam has a void volume of at least 50 volume %, preferably at least 70 volume %, more preferably at least 85 volume %, and even more preferably at least 95 volume %. In certain embodiments, the polymeric foam has a void volume of at most 99.9 volume %, preferably at most 99.5 volume %, more preferably at most 99 volume %, and even more preferably at most 98 volume %. For polymeric foams in which the bulk density of the polymer is typically near 1.0, foam densities can be closely correlated with void volumes.

In certain preferred embodiments, an assembly can further include a hardenable dental composition at least partially within the pores of a porous material. For such embodiments, at least 80 volume %, preferably at least 90 volume %, and more preferably 100 volume % of the void volume is filled with the hardenable dental composition.

For certain embodiments in which the compressible material is a porous foam (e.g., cellulose foams, glass foams, ceramic foams, polymeric foams, and combinations thereof), the foam can be prepared by a wide variety of methods known in the art. For example, porous foams can be prepared by incorporating one or more foaming agents into a material and activating the foaming agent(s). Foaming agents, also called blowing agents, can be used to foam plastics, rubbers, and thermoset resins to impart a cellular structure to the material. Chemical foaming agents form cells by decomposing to release gas when heated to their activation temperature. Physical blowing agents, on the other hand, are usually liquids at room temperature that volatilize when heated. Foams can also be prepared by dispersing bubbles or hollow capsules into the material, or using microspheres that encapsulate a physical blowing agent and expand into bubbles when heated. Alternatively, open-celled foams can be made by mixing a water-in-oil emulsion, either thermally or chemically polymerizing the oil phase, and then removing the water. For certain embodiments in which the compressible material is a porous foam, the porous foam can be prepared by foaming and optionally at least partially hardening a hardenable dental composition. For example, methacrylate-containing hardenable dental compositions can be foamed using hydrocarbon blowing agents (e.g., propane, isobutane, or combinations thereof such as a 1:1 mixture by weight of propane and isobutane).

For embodiments in which the compressible material includes capsules, the capsules are preferably hollow and can be ruptured by ordinary pressure encountered during application of the dental appliance to a tooth structure. Optionally, an assembly including capsules can further include a hardenable dental composition at least partially on an outer surface of the capsules. Optionally, an assembly including hollow capsules can further include a hardenable dental composition located at least partially within the capsules. Optionally, an assembly including hollow capsules can further include a liquid (e.g., aqueous or non-aqueous) inside at least a portion of the capsules. For example, an assembly including hollow capsules can further include water inside at least a portion of the capsules, which could be released when capsules are broken upon compression. Release of water upon compression could be useful for example, if the compressible material includes a water soluble or dispersible material (e.g., polyacrylic acid) that can be beneficial upon dissolution and/or dispersion. The release of water may also start an acid-base hardening reaction. Alternatively, the capsules may contain one half of a redox pair and begin the hardening reaction upon release. A wide variety of capsules can be used including, for example, microcapsules (i.e., capsules that typically have a diameter less than 10 micrometers), hollow glass beads (e.g., glass bubbles), hollow plastic beads, ceramic bubbles, and combinations thereof. Exemplary materials are disclosed, for example, in U.S. Pat. No. 4,303,730 (Torobin), U.S. Pat. No. 4,336,338 (Downs et al.), U.S. Pat. No. 5,045,569 (Delgado), and U.S. Pat. No. 5,861,214 (Kitano et al.).

Assemblies and methods of the present invention include a dental article and a compressible material. In certain embodiments, the assembly includes a layer of compressible material attached to a surface of the dental article. Dental articles having a compressible material attached to a surface thereof are to be distinguished from dental articles (e.g., precoated orthodontic appliances) having a release substrate (e.g., a release liner) on the precoated adhesive. In contrast to release substrates, which are designed to be removed before or during use of the article, a compressible material that is attached to a surface of a dental article is designed to remain on the dental article during use of the article, and in fact becomes a part of the bond upon applying the dental article and a hardenable dental composition to a tooth structure, and hardening the hardenable dental composition.

For embodiments of assemblies and methods of the present invention that include a dental article having an outer base surface and a compressible material, the compressible material can be of such size and shape that the compressible material can form a continuous layer on the outer base surface of the article. For alternative embodiments, the compressible material can be of such size and shape that it can form a discontinuous layer (e.g., a center hole) on the surface of the article.

The compressible material can form a layer having an area larger than the outer base surface of the article, coextensive with the outer base surface of the article, or smaller than the outer base surface of the article. For certain embodiments, a layer having an area smaller than the outer base surface of the article can be advantageously arranged on the outer base surface of the article to prevent the compressible material from extending beyond the outer base surface of the article upon compression.

The compressible material can optionally include two or more different materials that can be arranged as desired. For example, in certain embodiments, a mat or scrim can be made of two or more different types of fibers, wherein each type of fiber is distributed throughout the mat or scrim. In other embodiments, a mat or scrim can be made of two or more different types of fibers, wherein each type of fiber is not distributed throughout the mat or scrim. For example, one type of fiber can be substantially located in one layer (e.g., to form a denser material on the side adjacent the outer base surface of the article) and another type of fiber can be substantially located in another layer (e.g., to form a loftier material on the side adjacent the tooth surface). For another example, one type of fiber can be substantially located proximate the periphery of the mat or scrim (e.g., to form a denser material and/or to seal the edges of the compressible material), and another type of fiber can be substantially located proximate the center of the mat or scrim (e.g., to form a loftier material). For certain embodiments, different mats or scrims can be used for different teeth. For example, the mats or scrims used for molars may be loftier than the mats or scrims used for incisors. In certain embodiments, two or more appliances with different mats or scrims intended for use on different teeth can be combined in a single package similar to that described, for example, in U.S. Patent Application Publication No. 2006/0207893 (Cinader et al.).

An exemplary method of preparing a dental article having a compressible material attached to the base thereof is illustrated in FIGS. 1-4. This method includes two general steps: 1) coupling a compressible material to the dental article, and 2) charging the compressible material with a suitable unhardened dental composition.

Figure 4:
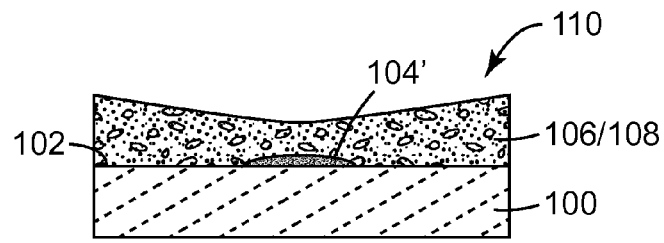
FIG. 4 is a side cross-sectional view showing the finished dental assembly referred to in FIGS. 1-3.

FIG. 1 shows the first step in making an exemplary dental assembly (broadly designated by the numeral 110 and shown finished in FIG. 4). In this step, a dental article 100 is provided. The dental article 100 has an outer base surface 102 adapted for bonding to a tooth structure. The dental article 100 can represent any one of a wide variety of bondable dental articles including, but not limited to, crowns, bridges, veneers, inlays, onlays, fillings, orthodontic appliances and devices, and prostheses (e.g., partial or full dentures). A droplet of a first quantity 104 of unhardened hardenable dental composition is selectively applied to a portion of the surface 102. As shown, the first quantity 104 extends over some, but not all, of the surface 102. Optionally and as shown, the first quantity 104 is in contact with a centrally located portion of the surface 102, without contacting portions of the surface 102 proximate to the edges of the dental article 100.

If desired, two or more quantities of the dental composition can be applied to the surface 102. For example, if the surface 102 was rectangular in shape, four discrete droplets of the unhardened composition may be applied, one at each corner of the surface 102. As shown, the diameter of the droplet of the first quantity 104 is relatively small compared to that of the surface 102.

In some embodiments, the droplet (or droplets) of the first quantity 104 extends over an area of the surface 102 that is at most 90%, at most 70%, at most 50%, at most 40%, at most 30%, at most 25%, at most 20%, at most 15%, at most 10%, or at most 5% of the total surface area of the surface 102 of the dental article 100. In some embodiments, the droplet of the first quantity 104 has an areal coverage that is at least 1%, at least 2%, at least 3%, at least 4%, at least 5%, at least most 7%, at least 10%, or at least 15% of the total surface area of the surface 102 of the dental article 100.

As further shown in FIG. 1, a porous compressible material 106 having first and second major surfaces 107, 109 is positioned over the surface 102 of the dental article 100. The pores in the compressible material 106 percolate (interconnect) through at least some of the compressible material 106 along directions perpendicular to the second major surface 109 of the compressible material 106. In this embodiment, the compressible material 106 comprises a translucent material, allowing the compressible material 106 to transmit actinic radiation. In some embodiments, and as shown here, the compressible material has a lateral size and shape that substantially matches that of the underlying surface 102. Preferably, the thickness of the compressible material 106 is sufficient to fill any gaps that might be present when the dental article 100 is seated against a tooth surface during a bonding.

Figure 2:
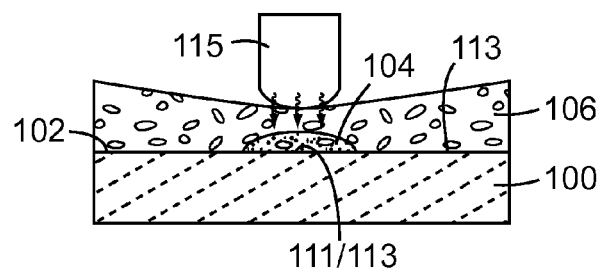
FIG. 2 is a side cross-sectional view showing a step in preparing an intermediary of the dental assembly referred to in FIG. 1.
Figure 3:
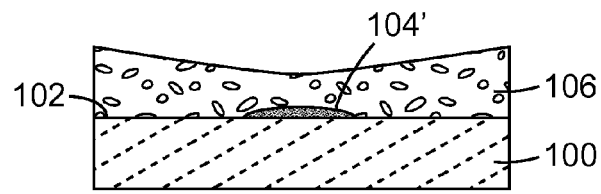
FIG. 3 is a side cross-sectional view showing the intermediary of the dental assembly referred to in FIGS. 1 and 2.

In the next step, shown in FIG. 2, the second major surface 109 of the compressible material 106 is placed in contact with the first quantity 104 as well as the surface 102 of the dental article 100. As the bottom of the compressible material 106 engages the dental article 100, the compressible material 106 is preferably at least partially compressed. Even if the compressible material 106 when relaxed does not match the surface 102, this step advantageously urges the compressible material 106 toward a configuration that is generally complemental to the surface 102, thereby enhancing the contact between these two components.

Optionally, and as shown in FIG. 2, placing the compressible material 106 in contact with the first quantity 104 causes essentially all of the first quantity 104 to be absorbed into the pores of the compressible material 106. In this configuration, an interfacial boundary 111 is formed between the first quantity 104 and the surface 102, which is generally shared with an interfacial boundary 113 formed between the compressible material 106 and the surface 102. In alternative embodiments, only some of the first quantity 104 absorbs into the compressible material 106 and some of the first quantity 104 is retained at the interface between the compressible material 106 and the dental article 100 or retained within undercut features present on the surface 102 of the dental article 100. In some embodiments, the first quantity 104 may be added to the compressible material 106 before or after the compressible material 106 is in contact with the surface 102.

After the compressible material 106 has been fully seated against the dental article 100, a curing light 115 is positioned above the first quantity 104 as also shown in FIG. 2. The curing light 115 then generates actinic radiation that is transmitted through the compressible material 106 to harden or partially harden the first quantity 104, providing the assembly shown in FIG. 3. The now-hardened first quantity 104' adhesively secures the compressible material 106 and the dental article 100 to each other. Notably, the hardened first quantity 104' may or may not extend completely traverse the thickness of the compressible material 106.

It is advantageous for the hardened first quantity 104' to extend across a relatively small portion of the total surface of the surface 102 of the dental article 100. In some embodiments, the hardened first quantity 104' extends across at most 90%, at most 70%, at most 50%, at most 40%, at most 30%, at most 25%, at most 20%, at most 15%, at most 10%, or at most 5% of the total surface area of the surface 102 of the dental article 100. In some embodiments, the hardened first quantity 104' extends across at least 1%, at least 2%, at least 3%, at least 4%, at least 5%, at least most 7%, at least 10%, or at least 15% of the total surface area of the surface 102 of the dental article 100.

The hardened first quantity 104' may be chemically bonded to one or both of the dental article 100 and the compressible material 106. As used herein, "chemically bonded" means bonded or attached through chemical means (e.g., via shared electron pairs such as covalent bonding, coordinate covalent bonding, acid-base interactions such as Brønsted-Lowry reactions, and the like, including combinations thereof). For example, a hardenable dental composition (e.g., a hardenable resin, glass ionomer, resin-modified glass ionomer, and/or epoxy) can be hardened to chemically bond the compressible material 106 to the surface 102 of the dental article 100.

The hardened first quantity 104' may also be mechanically bonded to both the compressible material 106 and the dental article 100. As used herein, "mechanically bonded" means bonded or attached through physical means (e.g., using hooks, loops, protrusions, van der Waals interactions, ionic bonds, and the like, including combinations thereof), and in certain embodiments utilizing the undercuts provided by mesh (e.g., on VICTORY SERIES brand brackets, 3M Unitek, Monrovia, Calif.) and glass grit (e.g., on ceramic brackets as described in U.S. Pat. No. 5,108,285 (Tuneberg)). For example, the hardened first quantity 104' could penetrate into both the compressible material 106 and undercuts located on the surface 102 of the dental article 100, thus enhancing mechanical retention between these components. In preferred embodiments, the absorption of the hardened first quantity 104' into the compressible material 106 results in an interpenetrating network.

Preferably, the majority of the hardened first quantity 104' is retained within the compressible material 106. As a surprising advantage of this method, use of a porous component such as the compressible material 106 allows the compressible material 106 to flatly engage the surface 102 adjacent the hardened first quantity 104'. Such a configuration helps to avoid the formation of unfilled gaps, and can assist in providing a stronger and more predictable bond. In some embodiments, at least 50 percent, at least 70 percent, at least 80 percent, at least 85 percent, at least 90 percent, at least 95 percent, or at least 97 percent of the hardened first quantity 104' is retained within the compressible material 106. Preferably, the portion of the hardened first quantity 104' not retained within the compressible material 106 is retained within undercut features present on the surface 102 of the dental article 100.

In the final step shown in FIG. 4, a second quantity 108 of unhardened hardenable dental composition is applied to the compressible material 106 to provide the completed dental assembly 110. As shown in the FIG. 4, the hardened first quantity 104' contacts a portion of the surface 102 that is centrally located with respect to the overall surface 102 as viewed from a direction perpendicular to the surface 102. The second quantity 108 fully surrounds the hardened first quantity 104' as viewed from a direction perpendicular to the surface 102. As an alternative, the second quantity 108 may only partially surround the hardened first quantity 104' as viewed from a direction perpendicular to the surface 102.

The second quantity 108 can be applied to all or a portion of compressible material 106 by methods known in the art including, but not limited to, coating, spraying, dipping, brushing, and the like. In some embodiments, the compressible material 106 is substantially saturated with the second quantity 108 such that the hardened first quantity 104' and unhardened second quantity 108 displace essentially all of the voids or pores contained in the compressible material 106.

In some embodiments, the first and second quantities 104,108 have chemical compositions that are essentially the same. Alternatively, the first and second quantities may be different but have similar compositions. For example, the first and second quantities 104,108 may both be derived from the same unfilled hardenable resin, such as TRANSBOND XT brand Primer (3M Unitek, Monrovia, Calif.). Alternatively, the first and second quantities 104,108 may be derived from the same general resin type but have different levels of filler loading. For example, one composition could be TRANSBOND XT brand Primer while the other could be TRANSBOND XT brand Light Cure Adhesive (3M Unitek, Monrovia, Calif.). In a preferred embodiment, the first quantity 104 has a filler loading greater than the filler loading of the second quantity 108. For example, the first quantity 104 could have a filler loading ranging from 60 to 90 weight percent based on the total weight of the first quantity 104, while the second quantity 108 could have a filler loading less than 60 weight percent based on the total weight of the second quantity 108.

The combination of the compressible material 106 and the first and second quantities 104,108, as described in the foregoing, are capable of securely fixing the article 100 to a tooth structure by a bond having sufficient strength to resist unintended detachment from the tooth structure.

Other options are possible. For example, the second quantity 108 can be applied to compressible material 106 substantially uniformly or non-uniformly. A hardenable dental composition can be patterned on compressible material 106. In some embodiments, the second quantity 108 could be one part of a two-part hardenable dental composition (e.g., a chemical cure primer), and the second part of the two-part hardenable dental composition can be applied to a tooth surface. In other embodiments, the second quantity 108 could include one part of a redox pair, and the other part of the redox pair can be applied to the second quantity 108 just prior to placement on the tooth.

In certain embodiments, attachment of the compressible material 106 to the surface 102 of the dental article 100 can be enhanced by a sandblasting treatment as described, for example, in Akin-Nergiz et al., *Fortschritte der Kieferorthopädie* (1995) 56(1):49-55; Atsu et al., *Angle Orthodontist* (2006) 76(5):857-862; Mujagic et al., *J. of Clinical Orthodontics* (2005) 39(6):375-382; Newman et al., *American J. of Orthodontics and Dentofacial Orthopedics* (1995) 108(3):237-241; and Wiechmann, *J. of Orofacial Orthopedics* (2000) 61(4):280-291. In brief, the treatment includes sandblasting the surface 102 with a silica-coated alumina sandblasting medium available under the trade designation Rocatec Plus from 3M, St. Paul, Minn. The sandblasting treatment can be carried out using, for example, a blasting module available under the trade designation Rocatec Jr. from 3M, St. Paul, Minn., with the module set at 2.8 bar for two to three seconds at a distance of one centimeter. A solution of silane (e.g., a silane in ethanol available under the trade designation 3M ESPE Sil from 3M, St. Paul, Minn.) can then be applied to the surface 102 and allowed to dry at room temperature for at least five minutes. The presence of silane on the surface 102 can further enhance the bonding of methacrylate-containing resins to the surface 102.

The assembly 110 can optionally include additional layer(s) of dental compositions (e.g., orthodontic adhesives, orthodontic primers, or combinations thereof, which are not illustrated in FIG. 4) in contact with compressible material 106. Specifically, such additional layer(s) can be between the surface 102 and compressible material 106, on compressible material 106 opposite surface 102, or both. Such layers may or may not cover the same area, and may independently be discontinuous (e.g., a patterned layer) or continuous (e.g., non-patterned) materials extending across all or a portion of the compressible material 106.

Figure 5:
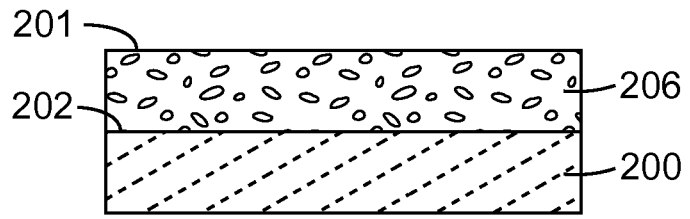
FIG. 5 is a side cross-sectional view of components of a dental assembly according to another embodiment of the invention.
Figure 6:
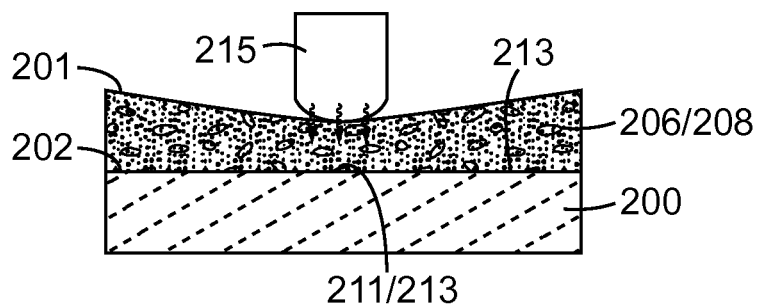
FIG. 6 is a side cross-sectional view showing a step in preparing the dental assembly referred to in FIG. 5.
Figure 7:
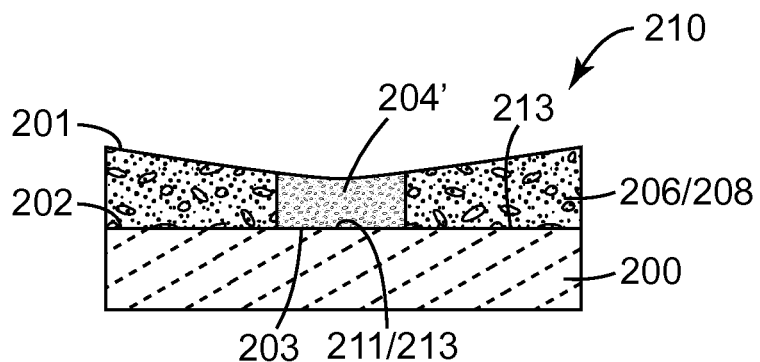
FIG. 7 is a side cross-sectional view showing the finished dental assembly referred to in FIGS. 5 and 6.

FIGS. 5-7 illustrate an exemplary method of making a dental assembly 210 (shown in FIG. 7) according to another embodiment. In the first step of the method, shown in FIG. 5, a dental article 200 and a compressible material 206 are provided. The dental article 200 has an outer base surface 202 adapted for bonding to a tooth, and the compressible material 206 having an exposed surface 201 contacts the dental article 200 along the surface 202.

In the second step, an unhardened hardenable dental composition 208 is applied to, and absorbed into, the compressible material 206 to provide the configuration shown in FIG. 6. Optionally and as shown, the unhardened composition 208 saturates the compressible material 206 such that it is also contacts the dental article 200 along the surface 202. In this saturated state, the compressible material 206 and the unhardened composition 208 are mutually coextensive. Preferably, the compressible material 206 and the unhardened composition 208 together form an interpenetrating network that generally occupies the same volume of space as its constituent components.

In the third step, also shown in FIG. 6, a curing light 215 transmits actinic radiation through the compressible material 206 to selectively harden the composition 208 over a local area 203 of the surface 202. As illustrated, the local area 203 is coextensive with the surface 202 and has a surface area less than that of the total surface area of the surface 202. Optionally and as shown, the curing light 215 at least partially compresses the compressible material 206 to limit the amount of light scattering and thereby avoid hardening the composition 208 over an unduly large area. Optionally, the selective hardening of the composition 208 may be achieved with improved precision using a curing light 215 that is a coherent light source, such as a laser. As another option, the actinic radiation may be directed through a masking element that selectively blocks the radiation to prevent hardening of the composition 208 not extending over the local area 203 of the surface 202.

The hardening of the unhardened composition 208 results in a hardened composition 204' (shown in FIG. 7 only), shaded to distinguish the hardened composition 204' from the quantity of dental composition 208 still unhardened. The hardened composition 204' extends out from the local area 203 of the surface 202 and terminates at the exposed surface 201. As illustrated, portions of the unhardened composition 208 not extending over the local area 203 remain unhardened and at least partially surround the hardened composition 204'. An interfacial boundary 211 is formed between the hardened composition 204' and the surface 202, which is generally shared with an interfacial boundary 213 formed between the compressible material 206 and the surface 202.

Figure 8:
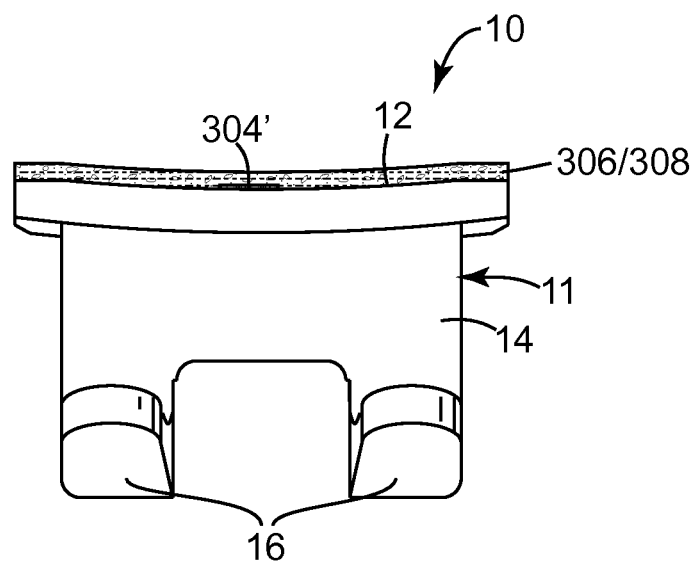
FIG. 8 is a side elevational view of a bondable orthodontic appliance according to still another embodiment of the invention.

FIG. 8 shows an exemplary embodiment of an assembly 10 that includes an appliance 11, in this case an orthodontic bracket. Other appliances such as buccal tubes, buttons, sheaths, bite openers, lingual retainers, bands, cleats, and other attachments are also contemplated. The appliance 11 includes a base 12, along with a body 14 that extends outwardly from the base 12. The base 12 can be a flange made of metal, plastic, glass, ceramic, or combinations thereof. The base 12 can include a mesh-like structure, such as a fine wire screen, or a molded base with undercut features. The base 12 can include particles (such as shards, grit, spheres, or other structure that optionally includes undercuts). Alternatively, the base 12 can be a custom base formed from one or more at least partially hardened dental composition layer(s). Four tiewings 16 are connected to the body 14, and an archwire slot 18 extends through a space between the tiewings 16.

The base 12, the body 14, and the tiewings 16 may be made of any one of a number of materials suitable for use in the oral cavity and having sufficient strength to withstand the correction forces applied during treatment. Suitable materials include, for example, metallic materials (such as stainless steel), ceramic materials (such as monocrystalline or polycrystalline alumina), and plastic materials (such as fiber-reinforced polycarbonate). Optionally, the base 12, the body 14, and the tiewings 16 are integrally made as a unitary component.

Extending across the base is a compressible material 306, hardened first quantity 304' of a dental composition and unhardened second quantity 308 of a dental composition. The compressible material 306 acts in combination with the first and second quantities 304',306 to securely fix the appliance 11 to the patient's tooth by a bond having sufficient strength to resist unintended detachment from the tooth during the course of treatment. Aspects, options, and advantages relating to the first and second quantities 304',306 and the compressible material 306 have been described with reference to dental assemblies 110,210 already and will not be repeated here.

Optionally, the manufacturer or supplier of the appliance 11 provides a hardenable dental composition pre-attached to the compressible material 306. In a preferred embodiment, the compressible material 306 is supplied having a hardenable dental composition therein. For embodiments in which the compressible material 306 is attached by the manufacturer to the base 12 of the appliance 11 and supplied as an assembly having a hardenable dental composition therein, it may be preferred to supply the assembly in a package or container that includes the article, as described herein.

Figure 9:
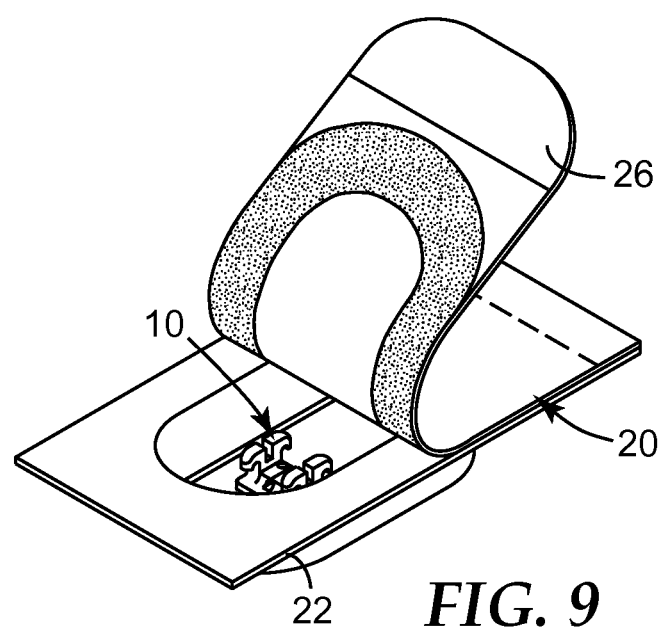
FIG. 9 is a perspective view of a packaged article according to yet another embodiment of the invention, the packaged article having a cover that is partially opened.

Exemplary containers are well known in the art and are disclosed, for example, in U.S. Pat. No. 5,172,809 (Jacobs et al.), U.S. Pat. No. 5,328,363 (Chester et al.) and U.S. Pat. No. 6,089,861 (Kelly et al.). Referring to FIG. 9, an exemplary embodiment of a packaged assembly 20 is shown including the assembly 10, which can include an orthodontic appliance that is the same or different than the exemplary embodiment illustrated in FIG. 8. The package 20 includes a container 22 and a cover 26. The cover 26, which is releasably connected to the container 22 as initially provided, is peeled from the container 22 to open the package for removal of the assembly 10. In FIG. 8, the cover 26 has been peeled back from the container 22 to partially open the packaged assembly 20.

In an alternative embodiment, the packaged assembly is an inverted blister with a foam member therein that contacts the tie wings such that the appliance 11 would be held in place and prevented from unduly sliding along lateral directions. For example, rather than contacting the bottom of the blister well, the appliance 11 can be positioned in the packaged assembly such that it rests on the cover 26, and foam can be placed in the bottom of the blister such that it contacts the tie wings 16 and holds the appliance 11 in place. Exemplary packaging concepts are described in the co-pending U.S. Patent Application Ser. No. 61/350,634 (Conley), filed on Jun. 2, 2010.

The external surface of the compressible material 306 optionally has a concave configuration, and optionally has a compound concave configuration, that inversely matches the convex configuration of the outer surface of the tooth intended for use with the appliance 11. As one example, the compressible material 306 may have a generally uniform thickness and the outer surface of the base 12 may have a concave configuration, such that the external surface of the compressible material when attached to the outer surface of the base 12 has a concave configuration that generally matches the concave configuration of the outer surface of the base 12. As another example, the outer surface of the base 12 may have a generally planar configuration that matches a generally planar configuration of a facing surface of the compressible material 306, while the external surface of the compressible material 306 may have a concave configuration that inversely matches the convex configuration of the tooth surface. Other constructions are also possible, including, for example, constructions in which the thickness of compressible material 306 varies corresponding to different position of the base.

As previously suggested, the assembly comprising the appliance 11 can optionally include additional layer(s) of dental compositions (e.g., orthodontic adhesives, orthodontic primers, or combinations thereof) in contact with compressible material 306. Specifically, such additional layer(s) can be between the base 12 and compressible material 306; on compressible material 306 opposite the base 12; or both. Such layers may or may not cover the same area, and may independently be discontinuous (e.g., a patterned layer) or continuous (e.g., non-patterned) materials extending across all or a portion of compressible material 306.

In preferred embodiments, the package provides excellent protection against degradation of optional hardenable dental composition(s) (e.g., photocurable materials), even after extended periods of time. Such containers are particularly useful for embodiments in which the optional hardenable dental composition optionally includes dyes that impart a color changing feature to the adhesive. Such containers preferably effectively block the passage of actinic radiation over a broad spectral range, and as a result, the optional dental compositions do not prematurely lose color during storage.

In preferred embodiments, the package includes a container 22 comprising a polymer and metallic particles. As an example, the container 22 may be made of polypropylene that is compounded with aluminum filler or receives an aluminum powder coating as disclosed, for example, in U.S. Patent Application Publication No. 2003/0196914 (Tzou et al.). The combination of polymer and metallic particles provides a highly effective block to the passage of actinic radiation to color changing dyes, even though such dyes are known to be highly sensitive to light. Such containers also exhibit good vapor barrier properties. As a result, the rheological characteristics of the hardenable dental composition(s) are less likely to change over extended periods of time. For example, the improved vapor barrier properties of such containers provide substantial protection against degradation of the handling characteristics of adhesives so that the dental compositions do not prematurely cure or dry or become otherwise unsatisfactory. Suitable covers 26 for such containers can be made of any material that is substantially opaque to the transmission of actinic radiation so that the dental compositions do not prematurely cure. Examples of suitable materials for cover 26 include laminates of aluminum foil and polymers. For example, the laminate may comprise a layer of polyethyleneterephthalate, adhesive, aluminum foil, adhesive and oriented polypropylene.

In some embodiments, a packaged assembly including an orthodontic appliance, a compressible material, and a hardenable dental composition may further include a release substrate as described, for example, in U.S. Pat. No. 6,183,249 (Brennan et al.).

In some embodiments, a package can include a set of assemblies including orthodontic appliances, wherein at least one of the assemblies includes an appliance having a compressible material thereon. Additional examples of assemblies (e.g., appliances) and sets of assemblies are described in U.S. Patent Publication No. 2005/0133384 (Cinader et al.). Packaged assemblies (e.g., orthodontic appliances) are described, for example, in U.S. Patent Publication No. 2003/0196914 (Tzou et al.) and U.S. Pat. No. 4,978,007 (Jacobs et al.), U.S. Pat. No. 5,015,180 (Randklev), U.S. Pat. No. 5,328,363 (Chester et al.), and U.S. Pat. No. 6,183,249 (Brennan et al.).

Dental Compositions

Hardenable dental compositions useful in assemblies and methods of the present invention typically include one or more hardenable components and a hardener. Optionally, hardenable dental compositions as described herein can include, for example, an initiator system, an ethylenically unsaturated compound, and/or one or more fillers. Hardenable and hardened dental compositions as described herein can be used for a variety of dental and orthodontic applications that utilize a material capable of adhering (e.g., bonding) to a tooth structure. Uses for such hardenable and hardened dental compositions include, for example, uses as adhesives (e.g., dental and/or orthodontic adhesives), cements (e.g., glass ionomer cements, resin-modified glass ionomer cements, and orthodontic cements), primers (e.g., orthodontic primers), restoratives, liners, sealants (e.g., orthodontic sealants), coatings, and combinations thereof.

Hardenable dental compositions (e.g., hardenable dental compositions) as described herein typically include a hardenable (e.g., polymerizable) component, thereby forming hardenable (e.g., polymerizable) compositions. The hardenable component can include a wide variety of chemistries, such as ethylenically unsaturated compounds (with or without acid functionality), epoxy (oxirane) resins, vinyl ethers, photopolymerization systems, redox cure systems, glass ionomer cements, polyethers, polysiloxanes, and the like. In some embodiments, the dental compositions can be hardened (e.g., polymerized by conventional photopolymerization and/or chemical polymerization techniques) prior to applying the hardened dental composition. In other embodiments, a dental composition can be hardened (e.g., polymerized by conventional photopolymerization and/or chemical polymerization techniques) after applying the hardenable dental composition.

In certain embodiments, the dental compositions are photopolymerizable, i.e., the dental compositions contain a photoinitiator (i.e., a photoinitiator system) that upon irradiation with actinic radiation initiates the polymerization (or hardening) of the dental composition. Such photopolymerizable compositions can be free radically polymerizable or cationically polymerizable. In other embodiments, the dental compositions are chemically hardenable, i.e., the dental compositions contain a chemical initiator (i.e., initiator system) that can polymerize, cure, or otherwise harden the dental composition without dependence on irradiation with actinic radiation. Such chemically hardenable dental compositions are sometimes referred to as "self-cure" compositions and may include glass ionomer cements (e.g., conventional and resin-modified glass ionomer cements), redox cure systems, and combinations thereof.

Suitable photopolymerizable components that can be used in the dental compositions as disclosed herein include, for example, epoxy resins (which contain cationically active epoxy groups), vinyl ether resins (which contain cationically active vinyl ether groups), ethylenically unsaturated compounds (which contain free radically active unsaturated groups, e.g., acrylates and methacrylates), and combinations thereof. Also suitable are polymerizable materials that contain both a cationically active functional group and a free radically active functional group in a single compound. Examples include epoxy-functional acrylates, epoxy-functional methacrylates, and combinations thereof.

Ethylenically Unsaturated Compounds

Dental compositions as disclosed herein may include one or more hardenable components in the form of ethylenically unsaturated compounds with or without acid functionality, thereby forming hardenable dental compositions.

Suitable hardenable dental compositions may include hardenable components (e.g., photopolymerizable compounds) that include ethylenically unsaturated compounds (which contain free radically active unsaturated groups). Examples of useful ethylenically unsaturated compounds include acrylic acid esters, methacrylic acid esters, hydroxy-functional acrylic acid esters, hydroxy-functional methacrylic acid esters, and combinations thereof.

The dental compositions (e.g., photopolymerizable compositions) may include compounds having free radically active functional groups that may include monomers, oligomers, and polymers having one or more ethylenically unsaturated group. Suitable compounds contain at least one ethylenically unsaturated bond and are capable of undergoing addition polymerization. Such free radically polymerizable compounds include mono-, di- or poly-(meth)acrylates (i.e., acrylates and methacrylates) such as, methyl (meth) acrylate, ethyl acrylate, isopropyl methacrylate, n-hexyl acrylate, stearyl acrylate, allyl acrylate, glycerol triacrylate, ethyleneglycol diacrylate, diethyleneglycol diacrylate, triethyleneglycol dimethacrylate, 1,3-propanediol di(meth) acrylate, trimethylolpropane triacrylate, 1,2,4-butanetriol trimethacrylate, 1,4-cyclohexanediol diacrylate, pentaerythritol tetra(meth)acrylate, sorbitol hexacrylate, tetrahydrofurfuryl (meth)acrylate, bis[1-(2-acryloxy)]-p-ethoxyphenyldimethylmethane, bis[1-(3-acryloxy-2-hydroxy)]-p-propoxyphenyldimethylmethane, ethoxylated bisphenol A di(meth)acrylate, and trishydroxyethyl-isocyanurate trimethacrylate; (meth)acrylamides (i.e., acrylamides and methacrylamides) such as (meth)acrylamide, methylene bis-(meth)acrylamide, and diacetone (meth)acrylamide; urethane (meth)acrylates; the bis-(meth)acrylates of polyethylene glycols (preferably of molecular weight 200-500), copolymerizable mixtures of acrylated monomers such as those in U.S. Pat. No. 4,652,274 (Boettcher et al.), acrylated oligomers such as those of U.S. Pat. No. 4,642,126 (Zador et al.), and poly(ethylenically unsaturated) carbamoyl isocyanurates such as those disclosed in U.S. Pat. No. 4,648,843 (Mitra); and vinyl compounds such as styrene, diallyl phthalate, divinyl succinate, divinyl adipate and divinyl phthalate. Other suitable free radically polymerizable compounds include siloxane-functional (meth)acrylates as disclosed, for example, in WO-00/38619 (Guggenberger et al.), WO-01/92271 (Weinmann et al.), WO-01/07444 (Guggenberger et al.), WO-00/42092 (Guggenberger et al.) and fluoropolymer-functional (meth)acrylates as disclosed, for example, in U.S. Pat. No. 5,076,844 (Fock et al.), U.S. Pat. No. 4,356,296 (Griffith et al.), EP-0373 384 (Wagenknecht et al.), EP-0201 031 (Reiners et al.), and EP-0201 778 (Reiners et al.). Mixtures of two or more free radically polymerizable compounds can be used if desired.

The hardenable component may also contain hydroxyl groups and ethylenically unsaturated groups in a single molecule. Examples of such materials include hydroxyalkyl (meth)acrylates, such as 2-hydroxyethyl (meth)acrylate and 2-hydroxypropyl (meth)acrylate; glycerol mono- or di-(meth)acrylate; trimethylolpropane mono- or di-(meth)acrylate; pentaerythritol mono-, di-, and tri-(meth)acrylate; sorbitol mono-, di-, tri-, tetra-, or penta-(meth)acrylate; and 2,2-bis[4-(2-hydroxy-3-ethacryloxypropoxy)phenyl]propane (bisGMA). Suitable ethylenically unsaturated compounds are also available from a wide variety of commercial sources, such as Sigma-Aldrich, St. Louis. Mixtures of ethylenically unsaturated compounds can be used if desired.

In certain embodiments hardenable components include PEGDMA (polyethyleneglycol dimethacrylate having a molecular weight of approximately 400), bisGMA, UDMA (urethane dimethacrylate), GDMA (glycerol dimethacrylate), TEGDMA (triethyleneglycol dimethacrylate), bisEMA6 as described in U.S. Pat. No. 6,030,606 (Holmes), and NPGDMA (neopentylglycol dimethacrylate). Various combinations of the hardenable components can be used if desired.

Preferably dental compositions as disclosed herein include at least 5% by weight, preferably at least 10% by weight, and more preferably at least 15% by weight ethylenically unsaturated compounds (e.g., with and/or without acid functionality), based on the total weight of the unfilled composition. Certain dental compositions as disclosed herein (e.g., unfilled dental compositions that consist of one or more ethylencially unsaturated compounds and an initiator system) can include 99% by weight or even higher of ethylenically unsaturated compounds (e.g., with and/or without acid functionality), based on the total weight of the unfilled composition. Other certain dental compositions as disclosed herein include at most 99% by weight, preferably at most 98% by weight, and more preferably at most 95% by weight ethylenically unsaturated compounds (e.g., with and/or without acid functionality), based on the total weight of the unfilled composition.

Ethylenically Unsaturated Compounds with Acid Functionality

Dental compositions as disclosed herein may include one or more hardenable components in the form of ethylenically unsaturated compounds with acid functionality, thereby forming hardenable dental compositions.

As used herein, ethylenically unsaturated compounds with acid functionality is meant to include monomers, oligomers, and polymers having ethylenic unsaturation and acid and/or acid-precursor functionality. Acid-precursor functionalities include, for example, anhydrides, acid halides, and pyrophosphates. The acid functionality can include carboxylic acid functionality, phosphoric acid functionality, phosphonic acid functionality, sulfonic acid functionality, or combinations thereof.

Ethylenically unsaturated compounds with acid functionality include, for example, α,β-unsaturated acidic compounds such as glycerol phosphate mono(meth)acrylates, glycerol phosphate di(meth)acrylates, hydroxyethyl (meth) acrylate (e.g., HEMA) phosphates, bis((meth)acryloxyethyl) phosphate, ((meth)acryloxypropyl) phosphate, bis((meth) acryloxypropyl) phosphate, bis((meth)acryloxy)propyloxy phosphate, (meth)acryloxyhexyl phosphate, bis((meth)acryloxyhexyl) phosphate, (meth)acryloxyoctyl phosphate, bis ((meth)acryloxyoctyl) phosphate, (meth)acryloxydecyl phosphate, bis((meth)acryloxydecyl) phosphate, caprolactone methacrylate phosphate, citric acid di- or tri-methacrylates, poly(meth)acrylated oligomaleic acid, poly(meth) acrylated polymaleic acid, poly(meth)acrylated poly(meth) acrylic acid, poly(meth)acrylated polycarboxyl-polyphosphonic acid, poly(meth)acrylated polychlorophosphoric acid, poly(meth)acrylated polysulfonate, poly(meth)acrylated polyboric acid, and the like, may be used as components in the hardenable component system. Also monomers, oligomers, and polymers of unsaturated carbonic acids such as (meth)acrylic acids, aromatic (meth)acrylated acids (e.g., methacrylated trimellitic acids), and anhydrides thereof can be used. Certain compositions for use in preferred methods of the present invention include an ethylenically unsaturated compound with acid functionality having at least one P—OH moiety.

Certain of these compounds are obtained, for example, as reaction products between isocyanatoalkyl (meth)acrylates and carboxylic acids. Additional compounds of this type having both acid-functional and ethylenically unsaturated components are described in U.S. Pat. No. 4,872,936 (Engelbrecht) and U.S. Pat. No. 5,130,347 (Mitra). A wide variety of such compounds containing both the ethylenically unsaturated and acid moieties can be used. Mixtures of such compounds can be used if desired.

Additional ethylenically unsaturated compounds with acid functionality include, for example, polymerizable bisphosphonic acids as disclosed for example, in U.S. Patent Publication No. 2004/0206932 (Abuelyaman et al.); AA:ITA:IEM (copolymer of acrylic acid:itaconic acid with pendent methacrylate made by reacting AA:ITA copolymer with sufficient 2-isocyanatoethyl methacrylate to convert a portion of the acid groups of the copolymer to pendent methacrylate groups as described, for example, in Example 11 of U.S. Pat. No. 5,130,347 (Mita)); and those recited in U.S. Pat. No. 4,259,075 (Yamauchi et al.), U.S. Pat. No. 4,499,251 (Omura et al.), U.S. Pat. No. 4,537,940 (Omura et al.), U.S. Pat. No. 4,539,382 (Omura et al.), U.S. Pat. No. 5,530,038 (Yamamoto et al.), U.S. Pat. No. 6,458,868 (Okada et al.), and European Patent Application Publication Nos. EP 712,622 (Tokuyama Corp.) and EP 1,051,961 (Kuraray Co., Ltd.).

Dental compositions as disclosed herein can also include compositions that include combinations of ethylenically unsaturated compounds with acid functionality. Preferably the dental compositions are self-adhesive and are non-aqueous. For example, such compositions can include: a first compound including at least one (meth)acryloxy group and at least one —O—P(O)(OH)$_x$ group, wherein x=1 or 2, and wherein the at least one —O—P(O)(OH)$_x$ group and the at least one (meth)acryloxy group are linked together by a C1-C4 hydrocarbon group; a second compound including at least one (meth)acryloxy group and at least one —O—P(O)(OH)$_x$ group, wherein x=1 or 2, and wherein the at least one —O—P(O)(OH)$_x$ group and the at least one (meth)acryloxy group are linked together by a C5-C12 hydrocarbon group; an ethylenically unsaturated compound without acid functionality; an initiator system; and a filler. Such compositions are described, for example, in Published U.S. Application No. 2007/0248927 (Luchterhandt et al.). See, also, U.S. Pat. No. 7,449,499 (Bradley et al.) and U.S. Pat. No. 7,452,924 (Aasen et al.); and Published U.S. Application Nos. 2005/0175966 (Falsafi et al.), 2009/0011388 (Bradley et al.), and 2009/0035728 (Aasen et al.).

Preferably dental compositions as disclosed herein include at least 5% by weight, preferably at least 10% by weight, and more preferably at least 15% by weight ethylenically unsaturated compounds with acid functionality, based on the total weight of the unfilled composition. Certain dental compositions as disclosed herein (e.g., unfilled dental compositions that consist of one or more ethylenically unsaturated compounds and an initiator system) can include 99% by weight or even higher of ethylenically unsaturated compounds with acid functionality, based on the total weight of the unfilled composition. Other certain dental compositions as disclosed herein include at most 99% by weight, preferably at most 98% by weight, and more preferably at most 95% by weight ethylenically unsaturated compounds with acid functionality, based on the total weight of the unfilled composition.

Epoxy (Oxirane) or Vinyl Ether Compounds

Hardenable dental compositions as disclosed herein may include one or more hardenable components in the form of epoxy (oxirane) compounds (which contain cationically active epoxy groups) or vinyl ether compounds (which contain cationically active vinyl ether groups), thereby forming hardenable dental compositions.

The epoxy or vinyl ether monomers can be used alone as the hardenable component in a dental composition or in combination with other monomer classes, e.g., ethylenically unsaturated compounds as described herein, and can include as part of their chemical structures aromatic groups, aliphatic groups, cycloaliphatic groups, and combinations thereof.

Examples of epoxy (oxirane) compounds include organic compounds having an oxirane ring that is polymerizable by ring opening. These materials include monomeric epoxy compounds and epoxides of the polymeric type and can be aliphatic, cycloaliphatic, aromatic or heterocyclic. These compounds generally have, on the average, at least 1 polymerizable epoxy group per molecule, in some embodiments at least 1.5, and in other embodiments at least 2 polymerizable epoxy groups per molecule. The polymeric epoxides include linear polymers having terminal epoxy groups (e.g., a diglycidyl ether of a polyoxyalkylene glycol), polymers having skeletal oxirane units (e.g., polybutadiene polyepoxide), and polymers having pendent epoxy groups (e.g., a glycidyl methacrylate polymer or copolymer). The epoxides may be pure compounds or may be mixtures of compounds containing one, two, or more epoxy groups per molecule. The "average" number of epoxy groups per molecule is determined by dividing the total number of epoxy groups in the epoxy-containing material by the total number of epoxy-containing molecules present.

These epoxy-containing materials may vary from low molecular weight monomeric materials to high molecular weight polymers and may vary greatly in the nature of their backbone and substituent groups. Illustrative of permissible substituent groups include halogens, ester groups, ethers, sulfonate groups, siloxane groups, carbosilane groups, nitro groups, phosphate groups, and the like. The molecular weight of the epoxy-containing materials may vary from 58 to 100,000 or more.

Suitable epoxy-containing materials useful as the resin system reactive components for use in methods of the present invention are listed in U.S. Pat. No. 6,187,836 (Oxman et al.) and U.S. Pat. No. 6,084,004 (Weinmann et al.).

Other suitable epoxy resins useful as the resin system reactive components include those which contain cyclohexene oxide groups such as epoxycyclohexanecarboxylates, typified by 3,4-epoxycyclohexylmethyl-3,4-epoxycyclohexanecarboxylate, 3,4-epoxy-2-methylcyclohexylmethyl-3,4-epoxy-2-methylcyclohexane carboxylate, and bis(3,4-epoxy-6-methylcyclohexyl-methyl) adipate. For a more detailed list of useful epoxides of this nature, reference is made to U.S. Pat. No. 6,245,828 (Weinmann et al.), U.S. Pat. No. 5,037,861 (Crivello et al), and U.S. Pat. No. 6,779,656 (Klettke et al.).

Other epoxy resins that may be useful in dental compositions as disclosed herein include glycidyl ether monomers. Examples are glycidyl ethers of polyhydric phenols obtained by reacting a polyhydric phenol with an excess of chlorohydrin such as epichlorohydrin (e.g., the diglycidyl ether of 2,2-bis-(2,3-epoxypropoxyphenol)propane). Further examples of epoxides of this type are described in U.S. Pat. No. 3,018,262 (Schroeder), and in "Handbook of Epoxy Resins" by Lee and Neville, McGraw-Hill Book Co., New York (1967).

Other suitable epoxides useful as the resin system reactive components are those that contain silicon, useful examples of which are described in International Patent Application Publication No. WO 01/51540 (Klettke et al.).

Additional suitable epoxides useful as the resin system reactive components include octadecylene oxide, epichlorohydrin, styrene oxide, vinyl cyclohexene oxide, glycidol, glycidylmethacrylate, diglycidyl ether of Bisphenol A and other commercially available epoxides, as provided in U.S. Pat. No. 7,262,228 (Oxman et al.).

Blends of various epoxy-containing materials are also contemplated. Examples of such blends include two or more weight average molecular weight distributions of epoxy-containing compounds, such as low molecular weight (below 200), intermediate molecular weight (200 to 10,000) and higher molecular weight (above 10,000). Alternatively or additionally, the epoxy resin may contain a blend of epoxy-containing materials having different chemical natures, such as aliphatic and aromatic, or functionalities, such as polar and non-polar.

Other types of useful hardenable components having cationically active functional groups include vinyl ethers, oxetanes, spiro-orthocarbonates, spiro-orthoesters, and the like.

If desired, both cationically active and free radically active functional groups may be contained in a single molecule. Such molecules may be obtained, for example, by reacting a di- or poly-epoxide with one or more equivalents of an ethylenically unsaturated carboxylic acid. An example of such a material is the reaction product of UVR-6105 (available from Union Carbide) with one equivalent of methacrylic acid. Commercially available materials having epoxy and free-radically active functionalities include the CYCLOMER series, such as CYCLOMER M-100, M-101, or A-200 available from Daicel Chemical, Japan, and EBECRYL-3605 available from Radcure Specialties, UCB Chemicals, Atlanta, Ga.

The cationically curable components may further include a hydroxyl-containing organic material. Suitable hydroxyl-containing materials may be any organic material having hydroxyl functionality of at least 1, and preferably at least 2. Preferably, the hydroxyl-containing material contains two or more primary or secondary aliphatic hydroxyl groups (i.e., the hydroxyl group is bonded directly to a non-aromatic carbon atom). The hydroxyl groups can be terminally situated, or they can be pendent from a polymer or copolymer. The molecular weight of the hydroxyl-containing organic material can vary from very low (e.g., 32) to very high (e.g., one million or more). Suitable hydroxyl-containing materials can have low molecular weights (i.e., from 32 to 200), intermediate molecular weights (i.e., from 200 to 10,000, or high molecular weights (i.e., above 10,000). As used herein, all molecular weights are weight average molecular weights.

The hydroxyl-containing materials may be non-aromatic in nature or may contain aromatic functionality. The hydroxyl-containing material may optionally contain heteroatoms in the backbone of the molecule, such as nitrogen, oxygen, sulfur, and the like. The hydroxyl-containing material may, for example, be selected from naturally occurring or synthetically prepared cellulosic materials. The hydroxyl-containing material should be substantially free of groups which may be thermally or photolytically unstable; that is, the material should not decompose or liberate volatile components at temperatures below 100° C. or in the presence of actinic light which may be encountered during the desired photopolymerization conditions for the polymerizable compositions.

Suitable hydroxyl-containing materials useful in methods of the present invention are listed in U.S. Pat. No. 6,187,836 (Oxman et al.).

The hardenable component(s) may also contain hydroxyl groups and cationically active functional groups in a single molecule. An example is a single molecule that includes both hydroxyl groups and epoxy groups.

Glass Ionomers

Hardenable dental compositions as described herein may include glass ionomer cements such as conventional glass ionomer cements that typically employ as their main ingredients a homopolymer or copolymer of an ethylenically unsaturated carboxylic acid (e.g., poly acrylic acid, copoly (acrylic, itaconic acid), and the like), a fluoroaluminosilicate ("FAS") glass, water, and a chelating agent such as tartaric acid. Conventional glass ionomers (i.e., glass ionomer cements) typically are supplied in powder/liquid formulations that are mixed just before use. The mixture will undergo self-hardening in the dark due to an ionic reaction between the acidic repeating units of the polycarboxylic acid and cations leached from the glass.

The glass ionomer cements may also include resin-modified glass ionomer ("RMGI") cements. Like a conventional glass ionomer, an RMGI cement employs an FAS glass. However, the organic portion of an RMGI is different. In one type of RMGI, the polycarboxylic acid is modified to replace or end-cap some of the acidic repeating units with pendent curable groups and a photoinitiator is added to provide a second cure mechanism, e.g., as described in U.S. Pat. No. 5,130,347 (Mitra). Acrylate or methacrylate groups are usually employed as the pendant curable group. In another type of RMGI, the cement includes a polycarboxylic acid, an acrylate or methacrylate-functional monomer and a photoinitiator, e.g., as in Mathis et al., "Properties of a New Glass Ionomer/Composite Resin Hybrid Restorative", Abstract No. 51, J. Dent Res., 66:113 (1987) and as in U.S. Pat. No. 5,063,257 (Akahane et al.), U.S. Pat. No. 5,520,725 (Kato et al.), U.S. Pat. No. 5,859,089 (Qian), U.S. Pat. No. 5,925,715 (Mitra), and U.S. Pat. No. 5,962,550 (Akahane et al.). In another type of RMGI, the cement may include a polycarboxylic acid, an acrylate or methacrylate-functional monomer, and a redox or other chemical cure system, e.g., as described in U.S. Pat. No. 5,154,762 (Mitra et al.), U.S. Pat. No. 5,520,725 (Kato et al.), and U.S. Pat. No. 5,871,360 (Kato). In another type of RMGI, the cement may include various monomer-containing or resin-containing components as described in U.S. Pat. No. 4,872,936 (Engelbrecht), U.S. Pat. No. 5,227,413 (Mitra), U.S. Pat. No. 5,367,002 (Huang et al.), and U.S. Pat. No. 5,965,632 (Orlowski). Dental compositions including such cements are able to harden in the dark due to the ionic reaction between the acidic repeating units of the polycarboxylic acid and cations leached from the glass, and commercial RMGI products typically also cure on exposure of the cement to light from a dental curing lamp. RMGI cements that contain a redox cure system and that can be cured in the dark without the use of actinic radiation are described in U.S. Pat. No. 6,765,038 (Mitra).

In certain embodiments, RMGI cements are formulated as powder/liquid or paste/paste systems, and contain water as mixed and applied. For embodiments in which the assembly includes a compressible material having the hardenable material applied thereto, water may be separated from the resin and filler. In other certain embodiments, cements having good shelf stability can be prepared by suspending water in the resin using an emulsifier to create a water-in-oil microemulsion. For other embodiments, in which the hardenable material contains no water, excess water present on the teeth can provide water for the bonding process. Fluoroaluminosilicate glass may be incorporated as an additional particulate filler or as a fibrous compressible material.

Photoinitiator Systems

In certain embodiments, the dental compositions of the present invention are photopolymerizable, i.e., the dental compositions contain a photopolymerizable component and a photoinitiator (i.e., a photoinitiator system) that upon irradiation with actinic radiation initiates the polymerization (or hardening) of the dental composition. Such photopolymerizable compositions can be free radically polymerizable or cationically polymerizable.

Suitable photoinitiators (i.e., photoinitiator systems that include one or more compounds) for polymerizing free radically photopolymerizable compositions include binary and tertiary systems. Typical tertiary photoinitiators include an iodonium salt, a photosensitizer, and an electron donor compound as described in U.S. Pat. No. 5,545,676 (Palazzotto et al.). Preferred iodonium salts are the diaryl iodonium salts, e.g., diphenyliodonium chloride, diphenyliodonium hexafluorophosphate, diphenyliodonium tetrafluoroborate, and tolylcumyliodonium tetrakis(pentafluorophenyl)borate. Preferred photosensitizers are monoketones and diketones that absorb some light within a range of 400 nm to 520 nm (preferably, 450 nm to 500 nm). More preferred compounds are alpha diketones that have some light absorption within a range of 400 nm to 520 nm (even more preferably, 450 to 500 nm). Preferred compounds are camphorquinone, benzil, furil, 3,3,6,6-tetramethylcyclohexanedione, phenanthraquinone, 1-phenyl-1,2-propanedione and other 1-aryl-2-alkyl-1,2-ethanediones, and cyclic alpha diketones. Most preferred is camphorquinone. Preferred electron donor compounds include substituted amines, e.g., ethyl dimethylaminobenzoate. Other suitable tertiary photoinitiator systems useful for photopolymerizing cationically polymerizable resins are described, for example, in U.S. Pat. No. 6,765,036 (Dede et al.).

Other suitable photoinitiators for polymerizing free radically photopolymerizable compositions include the class of phosphine oxides that typically have a functional wavelength range of 380 nm to 1200 nm. Preferred phosphine oxide free radical initiators with a functional wavelength range of 380 nm to 450 nm are acyl and bisacyl phosphine oxides such as those described in U.S. Pat. No. 4,298,738 (Lechtken et al.), U.S. Pat. No. 4,324,744 (Lechtken et al.), U.S. Pat. No. 4,385,109 (Lechtken et al.), U.S. Pat. No. 4,710,523 (Lechtken et al.), U.S. Pat. No. 4,737,593 (Enrich et al.), and U.S. Pat. No. 6,251,963 (Kohler et al.); and EP Application No. 0 173 567 A2 (Ying).

Commercially available phosphine oxide photoinitiators capable of free-radical initiation when irradiated at wavelength ranges of greater than 380 nm to 450 nm include bis(2,4,6-trimethylbenzoyl)phenyl phosphine oxide (IRGACURE 819, Ciba Specialty Chemicals, Tarrytown, N.Y.), bis(2,6-dimethoxybenzoyl)-(2,4,4-trimethylpentyl) phosphine oxide (CGI 403, Ciba Specialty Chemicals), a 25:75 mixture, by weight, of bis(2,6-dimethoxybenzoyl)-2,4,4-trimethylpentyl phosphine oxide and 2-hydroxy-2-methyl-1-phenylpropan-1-one (IRGACURE 1700, Ciba Specialty Chemicals), a 1:1 mixture, by weight, of bis(2,4,6-trimethylbenzoyl)phenyl phosphine oxide and 2-hydroxy-2-methyl-1-phenylpropane-1-one (DAROCUR 4265, Ciba Specialty Chemicals), and ethyl 2,4,6-trimethylbenzylphenyl phosphinate (LUCIRIN LR8893X, BASF Corp., Charlotte, N.C.).

Typically, the phosphine oxide initiator is present in the photopolymerizable composition in catalytically effective amounts, such as from 0.1 weight percent to 5.0 weight percent, based on the total weight of the dental composition.

Tertiary amine reducing agents may be used in combination with an acylphosphine oxide. Illustrative tertiary amines useful in the invention include ethyl 4-(N,N-dimethylamino) benzoate and N,N-dimethylaminoethyl methacrylate. When present, the amine reducing agent is present in the photopolymerizable composition in an amount from 0.1 weight percent to 5.0 weight percent, based on the total weight of the dental composition. Useful amounts of other initiators are well known to those of skill in the art.

Suitable photoinitiators for polymerizing cationically photopolymerizable compositions include binary and tertiary systems. Typical tertiary photoinitiators include an iodonium salt, a photosensitizer, and an electron donor compound as described in EP 0 897 710 (Weinmann et al.); in U.S. Pat. No. 5,856,373 (Kaisaki et al.), U.S. Pat. No. 6,084,004 (Weinmann et al.), U.S. Pat. No. 6,187,833 (Oxman et al.), U.S. Pat. No. 6,187,836 (Oxman et al.); and U.S. Pat. No. 6,765,036 (Dede et al.). The dental compositions of the invention can include one or more anthracene-based compounds as electron donors. In some embodiments, the dental compositions comprise multiple substituted anthracene compounds or a combination of a substituted anthracene compound with unsubstituted anthracene. The combination of these mixed-anthracene electron donors as part of a photoinitiator system provides significantly enhanced cure depth and cure speed and temperature insensitivity when compared to comparable single-donor photoinitiator systems in the same matrix. Such compositions with anthracene-based electron donors are described in U.S. Pat. No. 7,262,228 (Oxman et al.).

Suitable iodonium salts include tolylcumyliodonium tetrakis(pentafluorophenyl)borate, tolylcumyliodonium tetrakis(3,5-bis(trifluoromethyl)-phenyl)borate, and the diaryl iodonium salts, e.g., diphenyliodonium chloride, diphenyliodonium hexafluorophosphate, diphenyliodonium hexafluoroantimonate, and diphenyliodonium tetrafluoroboarate. Suitable photosensitizers are monoketones and diketones that absorb some light within a range of 450 nm to 520 nm (preferably, 450 nm to 500 nm). More suitable compounds are alpha diketones that have some light absorption within a range of 450 nm to 520 nm (even more preferably, 450 nm to 500 nm). Preferred compounds are camphorquinone, benzil, furil, 3,3,6,6-tetramethylcyclohexanedione, phenanthraquinone and other cyclic alpha diketones. Most preferred is camphorquinone. Suitable electron donor compounds include substituted amines, e.g., ethyl 4-(dimethylamino)benzoate and 2-butoxyethyl 4-(dimethylamino)benzoate; and polycondensed aromatic compounds (e.g. anthracene).

The initiator system is present in an amount sufficient to provide the desired rate of hardening (e.g., polymerizing and/or crosslinking). For a photoinitiator, this amount will be dependent in part on the light source, the thickness of the layer to be exposed to radiant energy, and the extinction coefficient of the photoinitiator. Preferably, the initiator system is present in a total amount of at least 0.01 weight percent, more preferably, at least 0.03 weight percent, and most preferably, at least 0.05 weight percent, based on the weight of the dental composition. Preferably, the initiator system is present in a total amount of no more than 10 weight percent, more preferably, no more than 5 weight percent, and most preferably, no more than 2.5 weight percent, based on the weight of the dental composition.

Redox Initiator Systems

In certain embodiments, the dental compositions of the present invention are chemically hardenable, i.e., the dental compositions contain a chemically hardenable component and a chemical initiator (i.e., initiator system) that can polymerize, cure, or otherwise harden the dental composition without dependence on irradiation with actinic radiation. Such chemically hardenable dental compositions are sometimes referred to as "self-cure" compositions and may include glass ionomer cements, resin-modified glass ionomer cements, redox cure systems, and combinations thereof.

The chemically hardenable dental compositions may include redox cure systems that include a hardenable component (e.g., an ethylenically unsaturated polymerizable component) and redox agents that include an oxidizing agent and a reducing agent. Suitable hardenable components, redox agents, optional acid-functional components, and optional fillers that are useful in the present invention are described in U.S. Pat. No. 7,173,074 (Mitra et al.) and U.S. Pat. No. 6,982,288 (Mitra et al.).

The reducing and oxidizing agents should react with or otherwise cooperate with one another to produce free-radicals capable of initiating polymerization of the resin system (e.g., the ethylenically unsaturated component). This type of cure is a dark reaction, that is, it is not dependent on the presence of light and can proceed in the absence of light. The reducing and oxidizing agents are preferably sufficiently shelf-stable and free of undesirable colorization to permit their storage and use under typical dental conditions. They should be sufficiently miscible with the resin system to permit ready dissolution in (and discourage separation from) the other components of the hardenable dental composition.

Useful reducing agents include ascorbic acid, ascorbic acid derivatives, and metal complexed ascorbic acid compounds as described in U.S. Pat. No. 5,501,727 (Wang et al.); amines, especially tertiary amines, such as 4-tert-butyl dimethylaniline; aromatic sulfinic salts, such as p-toluenesulfinic salts and benzenesulfinic salts; thioureas, such as 1-ethyl-2-thiourea, tetraethyl thiourea, tetramethyl thiourea, 1,1-dibutyl thiourea, and 1,3-dibutyl thiourea; and mixtures thereof. Other secondary reducing agents may include cobalt (II) chloride, ferrous chloride, ferrous sulfate, hydrazine, hydroxylamine (depending on the choice of oxidizing agent), salts of a dithionite or sulfite anion, and mixtures thereof. Preferably, the reducing agent is an amine.

Suitable oxidizing agents will also be familiar to those skilled in the art, and include but are not limited to persulfuric acid and salts thereof, such as sodium, potassium, ammonium, cesium, and alkyl ammonium salts. Additional oxidizing agents include peroxides such as benzoyl peroxides, hydroperoxides such as cumyl hydroperoxide, t-butyl hydroperoxide, and amyl hydroperoxide, as well as salts of transition metals such as cobalt (III) chloride and ferric chloride, cerium (IV) sulfate, perboric acid and salts thereof, permanganic acid and salts thereof, perphosphoric acid and salts thereof, and mixtures thereof.

It may be desirable to use more than one oxidizing agent or more than one reducing agent. Small quantities of transition metal compounds may also be added to accelerate the rate of redox cure. In some embodiments it may be preferred to include a secondary ionic salt to enhance the stability of the polymerizable composition as described in U.S. Pat. No. 6,982,288 (Mitra et al.).

The reducing and oxidizing agents are present in amounts sufficient to permit an adequate free-radical reaction rate. This can be evaluated by combining all of the ingredients of the hardenable dental composition except for the optional filler, and observing whether or not a hardened mass is obtained.

Preferably, the reducing agent is present in an amount of at least 0.01% by weight, and more preferably at least 0.1% by weight, based on the total weight (including water) of the components of the hardenable dental composition. Preferably, the reducing agent is present in an amount of no greater than 10% by weight, and more preferably no greater than 5% by weight, based on the total weight (including water) of the components of the hardenable dental composition.

Preferably, the oxidizing agent is present in an amount of at least 0.01% by weight, and more preferably at least 0.10% by weight, based on the total weight (including water) of the components of the hardenable dental composition. Preferably, the oxidizing agent is present in an amount of no greater than 10% by weight, and more preferably no greater than 5% by weight, based on the total weight (including water) of the components of the hardenable dental composition.

The reducing or oxidizing agents can be microencapsulated as described in U.S. Pat. No. 5,154,762 (Mitra et al.). This will generally enhance shelf stability of the hardenable dental composition, and if necessary permit packaging the reducing and oxidizing agents together. For example, through appropriate selection of an encapsulant, the oxidizing and reducing agents can be combined with an acid-functional component and optional filler and kept in a storage-stable state. Likewise, through appropriate selection of a water-insoluble encapsulant, the reducing and oxidizing agents can be combined with an FAS glass and water and maintained in a storage-stable state.

A redox cure system can be combined with other cure systems, e.g., with a hardenable dental composition such as described U.S. Pat. No. 5,154,762 (Mitra et al.).

Fillers

In certain preferred embodiments, the hardenable dental composition is unfilled. In other certain embodiments, the hardenable dental composition further includes a filler. Fillers can be selected from one or more of a wide variety of materials suitable for incorporation in compositions used for dental applications, such as fillers currently used in dental restorative compositions, and the like.

The filler is preferably finely divided. The filler can have a unimodal or polymodal (e.g., bimodal) particle size distribution. Preferably, the maximum particle size (the largest dimension of a particle, typically, the diameter) of the filler is less than 30 micrometers, more preferably less than 20 micrometers, and most preferably less than 10 micrometers. Preferably, the average particle size of the filler is less than 0.1 micrometers, and more preferably less than 0.075 micrometer.

The filler can be an inorganic material. It can also be a crosslinked organic material that is insoluble in the resin system (i.e., the hardenable components), and is optionally filled with inorganic filler. The filler should in any event be nontoxic and suitable for use in the mouth. The filler can be radiopaque or radiolucent. The filler typically is substantially insoluble in water.

Examples of suitable inorganic fillers are naturally occurring or synthetic materials including, but not limited to: quartz (i.e., silica, $SiO_2$); nitrides (e.g., silicon nitride); glasses and fillers derived from, for example, Zr, Sr, Ce, Sb, Sn, Ba, Zn, and Al; feldspar; borosilicate glass; kaolin; talc; zirconia; titania; low Mohs hardness fillers such as those described in U.S. Pat. No. 4,695,251 (Randklev); and submicron silica particles (e.g., pyrogenic silicas such as those available under the trade designations AEROSIL, including "OX 50," "130," "150" and "200" silicas from Degussa Corp., Akron, Ohio and CAB-O-SIL M5 silica from Cabot Corp., Tuscola, Ill.). Examples of suitable organic filler particles include filled or unfilled pulverized polycarbonates, polyepoxides, and the like. Further examples of fillers include soft fillers as described, for example, in International Application Publication Nos. WO 2010/039395 (Amos et al.) and WO 2009/045752 (Kalgutkar et al.).

Preferred non-acid-reactive filler particles are quartz (i.e., silica), submicron silica, zirconia, submicron zirconia, and non-vitreous microparticles of the type described in U.S. Pat. No. 4,503,169 (Randklev). Mixtures of these non-acid-reactive fillers are also contemplated, as well as combination fillers made from organic and inorganic materials.

The filler can also be an acid-reactive filler. Suitable acid-reactive fillers include metal oxides, glasses, and metal salts. Typical metal oxides include barium oxide, calcium oxide, magnesium oxide, and zinc oxide. Typical glasses include borate glasses, phosphate glasses, and fluoroaluminosilicate ("FAS") glasses. FAS glasses are particularly preferred. The FAS glass typically contains sufficient elutable cations so that a hardened dental composition will form when the glass is mixed with the components of the hardenable dental composition. The glass also typically contains sufficient elutable fluoride ions so that the hardened dental composition will have cariostatic properties. The glass can be made from a melt containing fluoride, alumina, and other glass-forming ingredients using techniques familiar to those skilled in the FAS glassmaking art. The FAS glass typically is in the form of particles that are sufficiently finely divided so that they can conveniently be mixed with the other cement components and will perform well when the resulting mixture is used in the mouth.

Generally, the average particle size (typically, diameter) for the FAS glass is no greater than 12 micrometers, typically no greater than 10 micrometers, and more typically no greater than 5 micrometers as measured using, for example, a sedimentation analyzer. Suitable FAS glasses will be familiar to those skilled in the art, and are available from a wide variety of commercial sources, and many are found in currently available glass ionomer cements such as those commercially available under the trade designations VITREMER, VITREBOND, RELY X LUTING CEMENT, RELY X LUTING PLUS CEMENT, PHOTAC-FIL QUICK, KETAC-MOLAR, and KETAC-FIL PLUS (3M ESPE Dental Products, St. Paul, Minn.), FUJI II LC and FUJI IX (G-C Dental Industrial Corp., Tokyo, Japan) and CHEMFIL Superior (Dentsply International, York, Pa.). Mixtures of fillers can be used if desired.

The surface of the filler particles can also be treated with a coupling agent in order to enhance the bond between the filler and the resin. The use of suitable coupling agents include gamma-methacryloxypropyltrimethoxysilane, gamma-mercaptopropyltriethoxysilane, gamma-aminopropyltrimethoxysilane, and the like. Silane-treated zirconia-silica ($ZrO_2$—$SiO_2$) filler, silane-treated silica filler, silane-treated zirconia filler, and combinations thereof are especially preferred in certain embodiments.

Other suitable fillers are disclosed in U.S. Pat. No. 6,387,981 (Zhang et al.) and U.S. Pat. No. 6,572,693 (Wu et al.) as well as International Patent Application Publication Nos. WO 01/30305 (Zhang et al.), WO 01/30306 (Windisch et al.), WO 01/30307 (Zhang et al.), and WO 03/063804 (Wu et al.). Filler components described in these references include nanosized silica particles, nanosized metal oxide particles, and combinations thereof. Nanofillers are also described in U.S. Pat. No. 7,090,721 (Craig et al.); U.S. Pat. No. 7,090,722 (Budd et al.); and U.S. Pat. No. 7,156,911 (Kangas et al.); and U.S. Published Application No. 2005/0256223 A1 (Kolb et al.).

For embodiments in which the hardenable dental composition includes one or more fillers, the hardenable dental composition preferably includes at least 1% by weight filler, more preferably at least 2% by weight filler, and most preferably at least 5% by weight filler. For embodiments in which the hardenable dental composition includes one or more fillers, the hardenable dental composition preferably includes at most 85% by weight filler, more preferably at most 50% by weight filler, and most preferably at most 25% by weight filler.

In certain preferred embodiments, unfilled or lightly filled hardenable dental compositions provide for easy cleanup of excess hardenable and/or hardened dental composition. Lightly filled hardenable dental compositions include at most 35% by weight filler, more preferably at most 20% by weight filler, and most preferably at most 10% by weight filler. Examples of unfilled and/or lightly filled hardenable dental compositions include primers and/or self-etching primers.

In certain preferred embodiments, the hardenable dental composition (e.g., filled or unfilled) is flowable during application, for example, at oral temperatures (e.g., 37° C.) in the methods described herein. As used herein, a "flowable" hardenable dental composition means that the dental composition deforms or flows under its own weight at oral temperatures (e.g., 37° C.). Certain "flowable" hardenable dental compositions deform or flow under their own weight at room temperature (e.g., 20-25° C.).

Optional Photobleachable and/or Thermochromic Dyes

In some embodiments, hardenable dental compositions of the present invention preferably have an initial color remarkably different than dental structures. Color is preferably imparted to the dental composition through the use of a photobleachable or thermochromic dye. The dental composition preferably includes at least 0.001% by weight photobleachable or thermochromic dye, and more preferably at least 0.002% by weight photobleachable or thermochromic dye, based on the total weight of the dental composition. The dental composition preferably includes at most 1% by weight photobleachable or thermochromic dye, and more preferably at most 0.1% by weight photobleachable or thermochromic dye, based on the total weight of the dental composition. The amount of photobleachable and/or thermochromic dye may vary depending on its extinction coefficient, the ability of the human eye to discern the initial color, and the desired color change. Suitable thermochromic dyes are disclosed, for example, in U.S. Pat. No. 6,670,436 (Burgath et al.).

For embodiments including a photobleachable dye, the color formation and bleaching characteristics of the photobleachable dye varies depending on a variety of factors including, for example, acid strength, dielectric constant, polarity, amount of oxygen, and moisture content in the atmosphere. However, the bleaching properties of the dye can be readily determined by irradiating the dental composition and evaluating the change in color. Preferably, at least one photobleachable dye is at least partially soluble in a hardenable resin.

Exemplary classes of photobleachable dyes are disclosed, for example, in U.S. Pat. No. 6,331,080 (Cole et al.), U.S. Pat. No. 6,444,725 (Trom et al.), and U.S. Pat. No. 6,528,555 (Nikutowski et al.). Preferred dyes include, for example, Rose Bengal, Methylene Violet, Methylene Blue, Fluorescein, Eosin Yellow, Eosin Y, Ethyl Eosin, Eosin bluish, Eosin B, Erythrosin B, Erythrosin Yellowish Blend, Toluidine Blue, 4',5'-Dibromofluorescein, and combinations thereof.

The color change in the inventive compositions is initiated by light. Preferably, the dental composition's color change is initiated using actinic radiation using, for example, a dental curing light which emits visible or near infrared (IR) light for a sufficient amount of time. The mechanism that initiates the color change in the dental compositions of the invention may be separate from or substantially simultaneous with the hardening mechanism that hardens the resin. For example, a composition may harden when polymerization is initiated chemically (e.g., redox initiation) or thermally, and the color change from an initial color to a final color may occur subsequent to the hardening process upon exposure to actinic radiation.

The change in composition color from an initial color to a final color is preferably quantified by a color test. Using a color test, a value of ΔE* is determined, which indicates the total color change in a 3-dimensional color space. The human eye can detect a color change of approximately 3 ΔE* units in normal lighting conditions. The dental compositions of the present invention are preferably capable of having a color change, ΔE*, of at least 20; more preferably, ΔE* is at least 30; most preferably ΔE* is at least 40.

Miscellaneous Optional Additives

Optionally, compositions of the present invention may contain solvents (e.g., alcohols (e.g., propanol, ethanol), ketones (e.g., acetone, methyl ethyl ketone), esters (e.g., ethyl acetate), other nonaqueous solvents (e.g., dimethylformamide, dimethylacetamide, dimethylsulfoxide, 1-methyl-2-pyrrolidinone)), and water.

If desired, the dental compositions of the invention can contain additives such as indicators, dyes, pigments, inhibitors, accelerators, viscosity modifiers, wetting agents, buffering agents, stabilizers, and other similar ingredients that will be apparent to those skilled in the art. Viscosity modifiers include the thermally responsive viscosity modifiers (such as PLURONIC F-127 and F-108 available from BASF Wyandotte Corporation, Parsippany, N.J.) and may optionally include a polymerizable moiety on the modifier or a polymerizable component different than the modifier. Such thermally responsive viscosity modifiers are described in U.S. Pat. No. 6,669,927 (Trom et al.) and U.S. Patent Application Publication No. 2004/0151691 (Oxman et al.).

Additionally, medicaments or other therapeutic substances can be optionally added to the dental compositions. Examples include, but are not limited to, fluoride sources, whitening agents, anticaries agents (e.g., xylitol), calcium sources, phosphorus sources, remineralizing agents (e.g., calcium phosphate compounds), enzymes, breath fresheners, anesthetics, clotting agents, acid neutralizers, chemotherapeutic agents, immune response modifiers, thixotropes, polyols, anti-inflammatory agents, antimicrobial agents (in addition to the antimicrobial lipid component), antifungal agents, agents for treating xerostomia, desensitizers, and the like, of the type often used in dental compositions. Combination of any of the above additives may also be employed. The selection and amount of any one such additive can be selected by one of skill in the art to accomplish the desired result without undue experimentation.

Bonding Methods

Dental articles (e.g., orthodontic appliances) having a compressible material attached to the surface thereof may be bonded to a tooth structure using methods (e.g., direct or indirect bonding methods) that are well known in the art.

Preferably, the compressible material 306 contains a hardenable dental composition 308 provided therein by the manufacturer. In another embodiment, the hardenable dental composition 308 can be added to compressible material 306 by a practitioner. For example, the practitioner can apply a hardenable dental composition 308 to compressible material 306, or compressible material 306 can be dipped or immersed in a hardenable dental composition 308.

A dental article (e.g., an orthodontic appliance) can be bonded to a tooth structure using compressible materials and hardenable dental compositions as described herein, using direct and/or indirect methods. Pursuant to the embodiment illustrated in FIG. 8, the assembly 10 is urged against a tooth structure until the base 12 of the appliance 11 is substantially seated against the tooth structure. The hardenable dental composition 308 is then hardened. During this procedure, the orthodontic appliance is applied to the tooth structure with sufficient pressure to substantially fill any gaps between the appliance and tooth structure.

Because the contour of the tooth structure surface may not precisely match the contour of the outer surface of the base 12, the compressible material 306 can be essentially completely compressed (e.g., at most 10% original pore volume remaining) in some areas, and essentially uncompressed (e.g., at least 90% of original pore volume remaining), or somewhat compressed in other areas. In certain embodiments, compressing compressible material 306 as completely as possible to minimize the distance between the appliance 11 and the tooth structure can be advantageous for accurately expressing the prescription of the appliance. For certain embodiments, compressible material 306 can have an initial (uncompressed) thickness of 0.8 millimeters (mm) (0.03 inch) to 2.5 mm (0.1 inch), and a compressed thickness in at least some portions of 0.12 mm (0.005 inch) to 0.25 mm (0.01 inch) (e.g., a compressed thickness that is 0.1 times the uncompressed thickness). Compressing compressible material 306 can cause excess hardenable dental composition 24 to exude from compressed compressible material 306 onto tooth structure 50 at or near the periphery of the appliance 11.

In some embodiments, pressure can be applied to the compressible material during hardening to prevent rebound of the compressible material. In other embodiments, the compressible material will remain compressed even after pressure is relieved.

The tooth structure can be untreated or treated. In some embodiments, the tooth structure is treated with a self-etching primer prior to contacting compressible material 306 with the tooth structure. For such embodiments, the hardenable dental composition can typically be hardened during or immediately after compressing the compressible material. In some embodiments, the hardenable dental composition is self-etching, and the tooth structure can be untreated prior to applying the appliance 11. For such embodiments, the hardenable dental composition preferably contacts the tooth structure for a period of time (e.g., 15 seconds or more) prior to hardening the hardenable dental composition. As an alternative, the tooth structure can be treated by phosphoric acid etching, followed by priming with a suitable orthodontic primer such as TRANSBOND XT brand primer or TRANSBOND MIP brand primer (both from 3M Unitek, Monrovia, Calif.).

Upon application of the appliance 11 to the tooth structure, the hardenable dental composition and/or compressible material (e.g., for embodiments in which the compressible material is, for example, a foamed and optionally partially hardened dental composition) can be hardened to adhere the orthodontic appliance to the tooth structure. A variety of suitable methods of hardening the dental composition are known in the art. For example, in some embodiments the hardenable dental composition can be hardened by exposure to UV or visible light. In other embodiments, the hardenable dental composition can be provided as a multi-part composition that hardens upon combining the two or more parts.

The compressible materials as described herein can be used for indirect bonding methods. For indirect bonding methods, orthodontic appliances can be placed, for example, on a model (e.g., replica plaster or "stone" model) of the patient's dental arch to provide a custom base for later mounting on the patient's tooth structure, commonly using a placement device. In one embodiment, the orthodontic appliances have a compressible material attached to the bases thereof for bonding to the replica plaster or "stone" model. Thus, the compressible material can be compressed to form a custom base, for example, upon hardening of a hardenable dental composition. Exemplary indirect bonding methods are described, for example, in U.S. Pat. No. 7,137,812 (Cleary et al.). In another embodiment, brackets are held in place on the model during formation of the placement device using a temporary adhesive, which can be washed away.

In another embodiment, an indirect bonding placement device can be formed about a rapid prototyping model (e.g., prepared by stereolithography, selective laser sintering, fused deposition modeling, and the like, or combinations thereof) of the patient's teeth with appliances attached. Such a rapid prototyping model can be produced from data supplied by a scan of an impression of the patient's teeth, a model of the patient's teeth, or of the teeth directly. Brackets can be held in place during formation of the placement device, for example, by a temporary adhesive or by friction fit with the guides as described, for example, in Published U.S. Patent Application No. 2006/0257821 (Cinader et al.). Compressible material can be added to the bracket bases following removal from the stereolithography model. For embodiments in which the brackets are held in place by friction fit with the placement guides, compressible material can be attached to the brackets prior to placement in the guides. If not already present, a hardenable dental composition can be added to the compressible material at any time from immediately following removal from the rapid prototyping model to immediately prior to placement in the patient's mouth.

In other embodiments of indirect bonding methods, the orthodontic appliance provided in the placement device can include a compressible material attached to a custom base such as a custom lingual appliance (which can optionally be formed from a compressed, compressible material) for bonding to a patient's tooth. Such embodiments are described in detail in U.S. Patent Publication No. 2009/0233252 (Cinader).

Advantageously, for embodiments in which the hardenable dental composition is unfilled or lightly filled, the practitioner may not need to remove excess dental composition (e.g., hardened or unhardened) from the tooth structure.

If removal of excess dental composition is desired, removal of unfilled or lightly filled dental composition (e.g., hardened or unhardened) can typically be effected by rinsing with water, applying toothpaste, brushing, or a combination thereof, by the practitioner or patient, which can reduce the risk of dislodging the appliance and/or damaging enamel that can be encountered during removal of excess highly filled hardened dental composition. In another embodiment, such excess unfilled or lightly filled hardenable or hardened dental composition can remain on the tooth as, for example, a sealant that can preferably provide additional protection to the tooth structure.

Objects and advantages of this invention are further illustrated by the following examples. Note however that the particular materials and amounts thereof recited in these examples, as well as other conditions and details, should not be construed to unduly limit this invention. Unless specified otherwise, all parts and percentages are by weight, all water is de-ionized water, all molecular weights are weight average molecular weight, and all chemicals and reagents were obtained from Sigma-Aldrich Corp., St. Louis, Mo.

EXAMPLES

As used herein:

"TBSLV" refers to an orthodontic adhesive available under the trade designation TRANSBOND Supreme LV brand Low Viscosity Light Cure Adhesive from 3M Unitek, Monrovia, Calif.

"TBXT Primer" refers to an unfilled orthodontic primer, available under the trade designation TRANSBOND XT brand Primer from 3M Unitek, Monrovia, Calif.

"TBXT Paste" refers to a filled orthodontic adhesive, available under the trade designation TRANSBOND XT brand Adhesive from 3M Unitek, Monrovia, Calif.

Fiber Pad Preparation

A meltblown web was made using B24 nylon resin from BASF SE (Ludwigshafen, Germany). A sample roll of nominally 20 inch (50.8 centimeter) wide web was collected under the conditions as follows. The polymer was extruded through a 20 inch (50.8 centimeter) wide drilled orifice die using a 1.5 inch single screw extruder operating at 22 pounds/hour (10 kilograms/hour) with a melt temperature of approximately 320° C. The die-to-collector distance was 6 inches (15.0 centimeters). A sample of the web was collected at a 44 grams/square meter basis weight and evaluated for effective fiber diameter according to the method set forth in Davies, C. N., "The Separation of Airborne Dust and Particles," Institution of Mechanical Engineers, London Proceedings 1B, 1952. The air temperature and velocity were adjusted to achieve the targeted effective fiber diameter of 5.5 microns.

Substrate Preparation

All test samples were prepared from uncut bovine teeth, which were cleaned and partially embedded in circular polymethylmethacrylate discs with the labial tooth surface exposed. All teeth were pumiced with fine powdered Italian pumice (obtained from Servalab, Inc., Maywood, N.J.), followed by rinsing with water and drying using an air syringe. The teeth were then etched and primed using 37% phosphoric acid (from 3M Unitek, Monrovia, Calif.) and TBXT Primer, respectively, prior to bonding.

Shear Peel Bond Strength Test Procedure

Shear peel bond strength was determined using the following standardized method. First, each bonded test specimen was mounted with the gingival tie wings oriented upward in a test fixture attached to a QTEST/5 brand mechanical testing machine (MTS Systems Corporation, Eden Prairie, Minn.). A 0.020 inch (0.051 centimeter) diameter standard round wire was looped under the occlusal tie wings and attached to the crosshead of the testing machine. After initial crosshead position was adjusted to make the wire snug, it was translated upward at 0.2 inches per minute (5 millimeters per minute) until the bracket was debonded. Maximum force was recorded and divided by the measured surface area of the bracket base to obtain a bond strength measurement. Each reported bond strength value represents an average of fifteen replicated measurements.

The remnant coverage was also determined based on the fracture surfaces observed under a microscope. This coverage was expressed as a percentage and reflects the area of hardened resin that was secured bound to the bonding base, divided by the overall bonding base area.

Rocatec Treatment in Examples 1-2 and Comparatives A and B

Examples 1-2 and Comparatives A and B used orthodontic bracket bonding bases treated using the Rocatec process. Each bonding base was sandblasted with a silica-coated alumina sandblasting medium available under the trade designation Rocatec Plus from 3M, St. Paul, Minn. The sandblasting treatment was carried out using a blasting module available under the trade designation Rocatec Jr. from 3M, St. Paul, Minn., with the module set at 2.8 bar for two to three seconds at a distance of about one centimeter. A solution of silane (e.g., a silane in ethanol available under the trade designation 3M ESPE Sil from 3M, St. Paul, Minn.) was then applied to the treated base surface and allowed to dry at room temperature for at least five minutes.

Examples 1-2

Examples 1-2 were prepared according to the following procedure. First, a spherical drop of binding resin having an approximate diameter of 1.3 millimeter (equivalent to about 1 milligram of binding resin) was precisely placed at the center of the bonding surface of a VICTORY SERIES brand stainless steel orthodontic bracket (upper left central bracket, part no. 017-401, from 3M Unitek, Monrovia, Calif.). Example 1 used TBSLV as a binding adhesive, while Example 2 used TBXT Paste as a binding adhesive. Second, a nylon fiber pad, having lateral dimensions slightly larger than that of the bonding surface, was pressed against the bonding surface, expressing the binding adhesive between the fiber pad and the mesh base of the bracket. The binding adhesive was then hardened by exposure to actinic radiation from an ORTHOLUX brand LED curing light (3M Unitek, Monrovia, Calif.) for 10 seconds. Using a pair of scissors, the fiber pad was then trimmed along the periphery of the bonding pad so that the fiber pad had the same size and shape as the bonding pad. Third, TBXT Primer was liberally applied to the porous fiber pad until the fiber pad was fully saturated.

Bonding was conducted for each test specimen by pressing the bracket-adhesive assembly against the tooth surface until it was fully seated against the tooth surface. The adhesive was then hardened by exposure to actinic radiation from the ORTHOLUX brand LED curing light for 10 seconds (5 seconds on each of the mesial and distal sides of the bracket).

Comparatives A-C

Comparatives A and B were prepared using VICTORY SERIES brand brackets with the same binding adhesives as those used in Examples 1 and 2, respectively. Unlike Examples 1 and 2, however, the binding adhesives of Comparatives A and B were not selectively applied to the bonding surface. Instead, an excess of the binding adhesive was applied uniformly across the entire bonding surface, and subsequently wiped off using straightedge such that the binding adhesive was maintained at a level approximately flush with the top surface of the mesh base. Subsequent steps, including saturation of the fiber pad with TBXT Primer and bonding to the tooth, were identical to those used in Examples 1 and 2.

Comparative C did not include a fiber pad, or any other compressible material. Instead, Comparative C used VICTORY SERIES brand brackets conventionally coated with TBXT Paste. As each bracket was mounted on its respective bovine tooth, the TBXT Paste coated the entire bonding surface and excess TBXT Paste extruded around the periphery of each bracket base. This excess adhesive was removed prior to hardening the TBXT Paste. Bonding proceeded as described above for Examples 1 and 2 and Comparatives A and B.

The shear peal bond strength and percentage of remnant coverage for Examples 1-2 and Comparatives A-C are shown in Table 1 below. In a two-sample T-test (performed on MINITAB brand 14 software, State College, Pa.), a significant difference in shear peel bond strength was determined between Example 2 and Comparative B. This significant difference was evidenced by a P-value of 0.041 between these two samples.

TABLE 1

Shear peel bond strength testing on Examples 1-2 and Comparatives A-C.

| Example/Comparative | Binding adhesive | Binding condition | Bond strength (MPa) | Remnant coverage |
|---|---|---|---|---|
| 1 | TBSLV | Spot | 14.62 ± 2.20 | 90% |
| 2 | TBXT Paste | Spot | 19.14 ± 2.21 | 100% |
| A | TBSLV | Full | 16.18 ± 3.36 | 64% |
| B | TBXT Paste | Full | 16.97 ± 3.21 | 90% |
| C | None | n/a | 20.16 ± 5.68 | n/a |

What is claimed is:

1. A method of making a dental assembly comprising:
   placing a compressible material in contact with an outer base surface of a dental article;
   applying a first quantity of an unhardened dental composition to at least one of the compressible material and the outer base surface in such a manner that at least some of the unhardened dental composition is located between the outer base surface and the compressible material;
   compressing at least a portion of the compressible material to urge the compressible material toward a configuration complemental to the outer base surface;
   hardening at least a portion of the first quantity of dental composition in order to secure the compressible material to the outer base surface while the compressible material is at least partially compressed, wherein at least part of the outer base surface is not in contact with the hardened dental composition; and
   applying a second quantity of unhardened dental composition to the compressible material, wherein the second quantity at least partially surrounds the hardened portion of the first quantity as viewed from a direction perpendicular to the outer base surface and is in contact with a portion of the outer base surface not in contact with the hardened dental composition.

2. The method of claim 1, wherein the act of applying a first quantity of an unhardened dental composition to at least one of the compressible material and the outer base surface is carried out before the compressible material is in contact with the outer base surface.

3. The method of claim 1, wherein the act of applying a first quantity of an unhardened dental composition to at least one of the compressible material and the outer base surface is carried out after the compressible material is in contact with the outer base surface.

4. The method of claim 1, wherein the first and second quantities have essentially the same chemical composition.

5. The method of claim 1, wherein the first quantity has a filler loading greater than the filler loading of the second quantity.

6. The method of claim 5, wherein the first quantity has a filler loading ranging from about 60 to 90 weight percent based on the total weight of the first quantity.

7. The method of claim 1, wherein the portion of the outer base surface is centrally located with respect to the outer base surface as viewed from a direction perpendicular to the outer base surface.

8. The method of claim 1, wherein the compressible material comprises a translucent material and hardening the first quantity comprises transmitting actinic radiation through at least some of the compressible material.

9. The method of claim 1, wherein placing the compressible material in contact with the outer base surface causes at least some of the first quantity to be absorbed into the compressible material thereby enhancing mechanical retention between the compressible material and the dental article when the first quantity is hardened, wherein at least 50 percent of the first quantity is absorbed into the compressible material.

10. The method of claim 9, wherein the absorption of the first quantity into the compressible material results in an interpenetrating network.

11. The method of claim 1, wherein the first quantity extends across about 2 percent to 30 percent of the outer base surface relative to the total area of the outer base surface after hardening.

12. A dental assembly comprising:
a dental article having an outer base surface adapted for bonding to a tooth;
a compressible material contacting and extending across at least a portion of the outer base surface;
a hardened dental composition absorbed into the compressible material and contacting a portion of the outer base surface that is less than the entire outer base surface; and
an unhardened dental composition absorbed into the compressible material and at least partially surrounding the hardened composition as viewed from a direction perpendicular to the outer base surface, wherein the unhardened dental composition is in contact with a portion of the outer base surface not in contact with the hardened dental composition.

13. The assembly of claim 12, wherein the hardened dental composition extends over about 2 percent to 30 percent of the outer base surface relative to the total area of the outer base surface.

14. The assembly of claim 12, wherein at least 50 percent of the hardened dental composition is absorbed into the compressible material.

* * * * *